US007244701B2

(12) United States Patent
Larsen et al.

(10) Patent No.: US 7,244,701 B2
(45) Date of Patent: Jul. 17, 2007

(54) DIURETIC PEPTIDE CONJUGATE

(75) Inventors: Bjarne Due Larsen, Roskilde (DK); Daniel R. Kapusta, Slidell, LA (US)

(73) Assignee: Zealand Phama A/S, Glostrup (DK)

( * ) Notice: Subject to any disclaimer, the term of this patent is extended or adjusted under 35 U.S.C. 154(b) by 16 days.

(21) Appl. No.: 09/882,291

(22) Filed: Jun. 15, 2001

(65) Prior Publication Data
US 2003/0040472 A1 Feb. 27, 2003

Related U.S. Application Data

(60) Provisional application No. 60/251,671, filed on Dec. 6, 2000, and provisional application No. 60/298,186, filed on Jun. 13, 2001.

(30) Foreign Application Priority Data

Jun. 16, 2000 (DK) .......................................... 2000 00944
Oct. 5, 2000 (DK) .......................................... 2000 01486

(51) Int. Cl.
*A61K 38/00* (2006.01)
*A61K 38/04* (2006.01)
*A61K 38/08* (2006.01)
*A61K 38/10* (2006.01)
*C07K 7/00* (2006.01)

(52) U.S. Cl. ........................... 514/2; 530/300; 530/326; 530/327; 530/328

(58) Field of Classification Search ...................... 514/2, 514/13, 313, 314, 322, 318, 25; 530/300, 530/326, 327, 328, 333, 330, 345; 540/171, 540/178, 159, 162, 194, 199; 504/14, 17, 504/18, 19
See application file for complete search history.

(56) References Cited

U.S. PATENT DOCUMENTS

| 5,688,772 | A | * | 11/1997 | Estrada et al. ................. 514/25 |
| 5,837,809 | A | * | 11/1998 | Grandy et al. .............. 530/326 |
| 5,840,696 | A | | 11/1998 | Lippton |
| 6,025,326 | A | * | 2/2000 | Steinberg et al. .............. 514/2 |
| 6,156,754 | A | * | 12/2000 | Lerchen et al. ........ 514/253.02 |
| 6,228,840 | B1 | * | 5/2001 | Wei et al. ..................... 514/16 |
| 6,387,628 | B1 | * | 5/2002 | Little et al. ..................... 435/6 |

FOREIGN PATENT DOCUMENTS

| DK | WO 99/44627 | * | 9/1999 |
| WO | WO 99/46283 |   | 9/1999 |
| WO | WO 01/98324 A1 |   | 12/2001 |
| WO | WO 02/26412 A1 |   | 4/2002 |

OTHER PUBLICATIONS

Dooley et al., "Binding and In Vitro Activities of Peptides with High Affinity for the Nociceptin/Orphanin FQ REceptor, ORL1," J. Pharmacol. Exp. Ther. 283: 735–741 (1997).*

D. Kapusta, et al. "Diuretic And Antinatriuretic Responses Produced By The Endogenous Opioid–like Peptide, Nociceptin (Orphanin FQ)", Life Sciences, 60: PL15–21, 1997.

D.R. Kapusta, et al. "Central Administration Of |Phe 1Ψ (CH 2– NH)Gly 2| Nociceptin (1–13)–NH 2 And Orphanin FQ/Nociceptin (OFQ/N) Produce Similar Cardiovascular And Renal Responses In Conscious Rats", J. Pharmacol. Exp. Therap. 289:173–180, 1999.

Daniel R. Kapusta, et al. "Cardiovascular And Renal Responses Produced By Central Orphanin FQ/Nociceptin Occur Independent Of Renal Nerves", Am. J. Physiol., 277:R987–R995, 1999.

D.R. Kapusta "Neurohumoral Effects Of Orphanin FQ/Nociceptin: Relevance To Cardiovascular And Renal Funtion", Peptides, 21:1081–1099, 2000.

D.R. Kapusta, et al. "Role Of The Renal Nerves In MediatingThe Renal Excretory Responses Produced By Central Administration Of The Opioid–Like Peptide, Nociceptin, In Conscious Rats", FASEB. J., 12:A364, 1998.

D.R. Kapusta, et al. "Central Nociceptin Produces Biphasic Changes In Urine Flow Rate In Conscious Rats Via ADH Dependent And Independent Mechanisms", Dept. Pharmacol. LSU Medical Center, New Orleans, LA 70112, and Phoenix Pharmaceuticals, Mountain View, CA 94043, FASEB J., 13:A457, 1999.

D.R. Kapusta, et al., "Nociceptin/Orphanin FQ Modulates The Cardiovascular And Renal Responses To Stress Differently Conscious Spontaneously Hypertensive Rats", FASEB J., 15:A1143, 2001.

D.R. Kapusta, et al. "Renal Responses To Central Administration Of Nociceptin (Orphanin FQ), A Novel Endogenous Opioid–Like Peptide", J. Amer. Soc. Nephrol. 7(9):1536, 1996.

D.R. Kapusta, et al. "Interaction Of Central mu Opioid And Nociceptin Systems In The Regulation Of Renal Excretory Function", FASEB J. 11:A250, 1997.

D.R. Kapusta, et al. "Central Administration Of A Proposed Nociceptin Receptor Antagonist Produces Nociceptin–Like Cardiovascular And Renal Responses", J.A.S.N. 9:308A, 1998.

L.A. Dayan, et al. "Central Injection Of Ro 64–6198, A Synthetic ORL1 Agonist, Produces Profound Nociceptin–Like Effects On Kidney Function And Feeding, But Not Cardiovascular Function", FASEB J. 15:A1143, 2001.

(Continued)

*Primary Examiner*—James C. Housel
*Assistant Examiner*—Zachariah Lucas
(74) *Attorney, Agent, or Firm*—Clark & Elbing LLP; Kristina Bieker-Brady

(57) ABSTRACT

Disclosed are a variety of peptide conjugates represented by the following general formula:

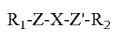

including methods of making and using such conjugates. Also provided are antibodies that specifically bind the peptide conjugates. The present invention has a wide spectrum of important applications including use in the treatment of disorders impacted by nociceptin and related opioid-like peptides.

19 Claims, 10 Drawing Sheets

OTHER PUBLICATIONS

Velga A. Kenigs, et al. "[Nphe 1] Nociceptin(1–13)NH2 Antagonizes The Cardiovascular Responses To Peripheral, But Not Central Administration Of Nociceptin/orphanin FQ In Conscious Rats", FASEB J. 15:A1142, 2001.

Lapalu et al. "Comparison of the Structure–Activity Relationships of Nociceptin and Dynorphin A Using Chimeric Peptides," *FEBS Letters*, 417(3):333–336 (1997).

Meunier et al. "The Nociceptin (ORL1) Receptor: Molecular Cloning and Functional Architecture," *Peptides* 21(7):893–900 (2000).

Rizzi et al. "Pharmacological Characterization of the Novel Nociceptin/Orphanin FQ Receptor Ligand, ZP120: In Vitro and In Vivo Studies in Mice," *British J. Pharmacol.* 137:369–374 (2002).

* cited by examiner

SEQUENCE LISTING

<160> NUMBER OF SEQ ID NOS: 77

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 1

Arg Tyr Tyr Arg Trp Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 2

Lys Tyr Tyr Arg Trp Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 3

Arg Tyr Tyr Arg Trp Arg
1               5

<210> SEQ ID NO 4
<211> LENGTH: 6
<212> TYPE: PRT
<213> ORGANISM: Artificial Sequence

```
<220> FEATURE:
<223> OTHER INFORMATION: Description of Artificial Sequence:
      synthetic peptide sequence

<400> SEQUENCE: 4

Lys Trp Arg Tyr Tyr Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 5

Arg Tyr Tyr Arg Ile Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 6

Arg Tyr Tyr Arg Ile Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 7

Arg Tyr Tyr Lys Ile Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 8

Arg Tyr Tyr Lys Ile Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 9

Arg Tyr Tyr Lys Trp Arg
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 10

Arg Tyr Tyr Lys Trp Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 11

Lys Tyr Tyr Arg Trp Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 12

Asn Glu Glu Glu Glu Glu Glu Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 13

Asn Glu Glu Glu Glu Glu Glu
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 14

Asn Glu Glu Glu Glu Glu
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:
      synthetic peptide sequence
```

```
<400> SEQUENCE: 15

Asn Glu Glu Glu
1

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 16

Ser Glu Glu Glu Glu Glu Glu Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 17

Ser Glu Glu Glu Glu Glu Glu
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 18

Ser Glu Glu Glu Glu Glu
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 19

Ser Glu Glu Glu
1

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 20

Asn Pro Glu Glu Glu Glu
1               5

<210> SEQ ID NO 21
<211> LENGTH: 7
<212> TYPE: PRT
```

```
<213> ORGANISM: Artificial Sequence
<220> FEATURE:
<223> OTHER INFORMATION: Description of Artificial Sequence:
      synthetic peptide sequence

<400> SEQUENCE: 21

Asn Pro Glu Glu Glu Glu Glu
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 22

Asn Asp Asp Asp Asp Asp Asp
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 23

Asn Asp Asp Asp Asp Asp Asp
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 24

Asn Asp Asp Asp Asp Asp
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 25

Asn Asp Asp Asp
1

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 26

Gln Glu Glu Glu Glu Glu Glu Glu
1               5
```

```
<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 27

Gln Glu Glu Glu Glu Glu
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 28

Gln Glu Glu Glu
1

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 29

Gln Asn Asp Asp Asp Asp Asp Asp Asp
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 30

Gln Asp Asp Asp Asp Asp Asp
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 31

Gln Asp Asp Asp Asp Asp
1               5

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:
      synthetic peptide sequence
```

```
<400> SEQUENCE: 32

Gln Asp Asp Asp
1

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 33

Asn Glu Glu Glu Glu Glu Arg Tyr Tyr Arg Trp Lys Lys Lys Lys
1               5                  10                  15

Lys Lys

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 34

Asn Glu Glu Glu Glu Glu Arg Tyr Tyr Arg Trp Lys
1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 35

Arg Tyr Tyr Arg Trp Lys Lys Lys Lys Lys Lys Lys
1               5                  10

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 36

Asn Glu Glu Glu Glu Glu Arg Tyr Tyr Arg Trp Arg Lys Lys Lys Lys
1               5                  10                  15

Lys Lys

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 37

Asn Glu Glu Glu Glu Glu Arg Tyr Tyr Arg Trp Arg
1               5                  10
```

```
<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 38

Arg Tyr Tyr Arg Trp Arg Lys Lys Lys Lys Lys Lys
1               5                  10

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 39

Asn Glu Glu Glu Glu Glu Arg Tyr Tyr Arg Ile Lys Lys Lys Lys
1               5                  10                  15

Lys Lys

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 40

Asn Glu Glu Glu Glu Glu Arg Tyr Tyr Arg Ile Lys
1               5                  10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 41

Arg Tyr Tyr Arg Ile Lys Lys Lys Lys Lys Lys
1               5                  10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 42

Lys Lys Lys Lys Lys Lys Arg Tyr Tyr Arg Trp Lys
1               5                  10

<210> SEQ ID NO 43
<211> LENGTH: 11
<212> TYPE: PRT
<213> ORGANISM: Artificial Sequence
<220> FEATURE:
```

```
<223> OTHER INFORMATION: Description of Artificial Sequence:
      synthetic peptide sequence

<400> SEQUENCE: 43

Tyr Gly Arg Lys Lys Arg Arg Gln Arg Arg
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 44

Tyr Ala Arg Lys Ala Arg Arg Gln Ala Arg Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 45

Tyr Ala Arg Ala Ala Ala Arg Gln Ala Arg Ala
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 46

Tyr Ala Arg Ala Ala Arg Arg Ala Ala Arg Arg
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 47

Tyr Ala Arg Ala Ala Arg Arg Ala Ala Arg Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 48

Ala Arg Arg Arg Arg Arg Arg Arg Arg Arg
1               5                   10
```

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 49

Tyr Ala Ala Ala Arg Arg Arg Arg Arg Arg
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 50

Arg Tyr Asn Arg Trp Lys Lys Lys Lys Lys Lys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 51

Lys Lys Lys Lys Lys Lys Lys Trp Arg Tyr Tyr Asn
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 52

Lys Lys Lys Lys Lys Lys Lys Trp Arg Tyr Tyr Arg
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 53

Lys Tyr Tyr Arg Trp Lys Lys Lys Lys Lys Lys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 54

Arg Tyr Tyr Arg Trp Lys Ala Lys Lys Lys Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 55

Arg Tyr Tyr Arg Trp Lys Lys Lys Lys Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 56

Arg Tyr Tyr Arg Trp Lys Lys Lys Lys Lys Lys Cys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 57

Lys Trp Arg Tyr Tyr Asn Lys Lys Lys Lys Lys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 58

Lys Trp Arg Tyr Tyr Arg Lys Lys Lys Lys Lys
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 59

Arg Tyr Tyr Arg Trp Lys Cys
1               5

<210> SEQ ID NO 60
<211> LENGTH: 7
<212> TYPE: PRT
<213> ORGANISM: Artificial Sequence

```
<220> FEATURE:
<223> OTHER INFORMATION: Description of Artificial Sequence:
      synthetic peptide sequence

<400> SEQUENCE: 60

Lys Tyr Tyr Arg Trp Lys Cys
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 61

Cys Trp Lys Lys Lys Lys Lys Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 62

Cys Lys Lys Lys Lys Lys Lys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 63

Cys Trp Lys Lys Lys Lys Lys Lys
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 64

Cys Ala Pro Pro Ser Lys Lys Lys Lys Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 65

Cys Ala Ala Pro Lys Lys Lys Lys Lys Lys
1               5                   10
```

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 66

Cys Pro Pro Ser Lys Lys Lys Lys Lys
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 67

Arg Lys Lys Arg Arg Gln Arg Arg Arg
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 68

Ala Lys Lys Lys Lys Gly
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 69

Lys Lys Lys Lys Lys Gly
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 70

Ala Lys Lys Lys Lys Lys
1               5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence:
      synthetic peptide sequence

```
<400> SEQUENCE: 71

Lys Lys Lys Lys Lys Lys Lys Lys Lys Lys
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 72

Lys Lys Lys Lys Lys Lys Lys Lys Lys
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 73

Lys Lys Lys Lys Lys Lys Lys Lys
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 74

Lys Lys Lys Lys Lys Lys Lys
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 75

Lys Lys Lys Lys Lys Lys
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence:
      synthetic peptide sequence

<400> SEQUENCE: 76

Lys Lys Lys Lys Lys
1               5

<210> SEQ ID NO 77
<211> LENGTH: 4
<212> TYPE: PRT
```

```
<213> ORGANISM: Artificial Sequence
<220> FEATURE:
<223> OTHER INFORMATION: Description of Artificial Sequence:
      synthetic peptide sequence

<400> SEQUENCE: 77

Lys Lys Lys Lys
1
```

DIURETIC PEPTIDE CONJUGATE

CROSS-REFERENCE TO RELATED APPLICATIONS

The present application claims the benefit of U.S. Provisional Application No. 60/298,186 entitled *Novel Peptide Conjugates* filed on Jun. 13, 2001 by Larsen, B. D. et al.. The instant application claims further benefit to U.S. Provisional Application No. 60/251,671 filed on Dec. 6, 2000. The present application claims additional benefit to Danish Patent Applications DK PA2000 01485 filed on Oct. 5, 2000 and DK PA2000 00944 filed on Jun. 16, 2000. The disclosures of said U.S. Provisional Application No. 60/298,186; 60/251,671; DK PA2000 01485; and DK PA2000 00944 applications are each incorporated herein by reference.

FIELD OF THE INVENTION

The present invention relates to novel peptide conjugates having interesting pharmacological activities, a method of preparing the novel peptide conjugates, pharmaceutical compositions containing the peptide conjugates, and the use of the peptide conjugates for the preparation of a medicament.

BACKGROUND

The endogenous opioid-like peptide, nociceptin (also referred to as orphanin FQ), was first described in the central nervous system, and most research in this field has focused on the CNS effects. Nociceptin binds to a specific receptor named opioid receptor-like one (ORL1) with much greater affinity than to the three classical subtypes of opioid receptors. Effects of nociceptin in the CNS include: hyperalgesia/hypoalgesia, stimulation of appetite and gnawing, increased (low doses) or decreased (high doses) locomotion, impaired learning, and dysphoria. However, nociceptin also exerts important effects outside the CNS. Thus, low doses of nociceptin increase the renal excretion of water and decrease urinary sodium excretion (i.e., produces a selective water diuresis) which render this compound interesting for the treatment of hyponatremia (Daniel R. Kapusta, Life Science, 60:15–21, 1997) (U.S. Pat. No. 5,840,696). When administered centrally (i.c.v.) or at high doses peripherally (i.v. bolus or infusion), nociceptin decreases blood pressure, heart rate and peripheral sympathetic nerve activity.

Dooley et al. (The Journal of Pharmacology and Experimental Therapeutics, 283(2):735–741, 1997) have shown that a positively charged hexapeptide having the amino acid sequence Ac-RYY(RK)(WI)(RK)-NH$_2$, where the brackets show allowable variation of amino acid residue, acts as a partial agonist of the nociceptin receptor ORL1. Said hexapeptide was identified from a combinatorial peptide library and the sequence is unique without homology or similarity to the nociceptin heptadecapeptide. However, said hexapeptide is too unstable to yield a satisfactory medicament.

WO 99/44627 discloses the use of hexapeptides including the hexapeptides discovered by Dooley et al. for the manufacture of a pharmaceutical composition for the treatment of the following conditions: Migraine, type II diabetes, septic shock, inflammation and vasomotor disturbances. It is shown that the hexapeptide Ac-Arg-Tyr-Tyr-Arg-Trp-Lys-NH$_2$ inhibits depressor response to spinal cord stimulation.

Considering that ORL1 agonists including the hexapeptide discovered by Dooley et al. as well as true nociceptin analogues are expected to have serious CNS side effects, if exposed to the brain, which are observed at dose levels higher than those required to elicit water diuresis in rats, it is a major objective of the present invention to provide novel conjugated peptides having the nociceptin-like activity of said hexapeptide or binding activity at the ORL1 receptor, but acting selectively outside the CNS. It is a further object of the invention to provide novel conjugated peptides having the nociceptin-like activity of said hexapeptide or binding activity at the ORL1 receptor and having improved stability. Moreover, it is an object of the invention to provide novel conjugated peptides having nociceptin-like activity or binding activity at the ORL1 receptor and/or at a yet unidentified receptor in kidney tissue.

This objective is achieved with the peptide conjugates of the present invention comprising hexapeptides modified C- and/or N-terminally by conjugation to short charged peptide chains.

SUMMARY OF THE INVENTION

A peptide conjugate of the general formula I

$$R_1\text{-}Z\text{-}X\text{-}Z'\text{-}R_2 \qquad (I)$$

wherein X represents a hexapeptide of the formula II

$$A^1\text{-}A^2\text{-}A^3\text{-}A^4\text{-}A^5\text{-}A^6 \qquad (II)$$

wherein $A^1$ represents Arg, Lys, His or Asp, $A^2$ represents Tyr, Trp, or Phe, $A^3$ represents Tyr, Asn, Trp or Phe, $A^4$ represents Lys, Arg or His, $A^5$ represents Phe, Tyr, Trp, Leu, Val or Ile, and $A^6$ represents Arg, Lys or His and wherein each amino acid residue in said hexapeptide may be in the L or D form;

Z represents a charged peptide chain of from 4 to 20 amino acid residues having the D or L configuration or is missing; and Z' represents a charged peptide chain of from 4 to 20 amino acid residues having the D or L configuration or is missing, providing that not both of Z and Z' are missing;

$R_1$ represents H or an acyl group;

$R_2$ represents $NR_3R_4$ where each of $R_3$ and $R_4$ independently represents hydrogen, C(1–6)-alkoxy, aryloxy or a lower alkyl as defined herein; or $R_2$ represents OH; and salts, hydrates and solvates thereof and C-terminally amidated or esterified derivatives thereof with suitable organic or inorganic acids.

The peptide conjugates of the invention can form acid addition salts, preferably with pharmaceutically acceptable acids, and these salts are included within the scope of the invention. The compounds may serve as medicaments in their pure form. However, the compounds are preferably incorporated into either solid or liquid medical formulations including tablets, capsules, solutions and suspensions. Other components of such formulations can include, a carrier, a diluent, a buffering agent, a tonicity adjusting agent and a preservative. Solid formulations are particularly suitable for oral administration, while solutions are most useful for injection (i.v., i.m., i.p. or s.c.) or intranasal administration.

The peptide conjugates of the invention having nociceptin-like activity or binding activity at the ORL1 receptor, but acting outside the CNS, are especially useful in the treatment of ORL1 related peripheral diseases and ailments, such as diseases where a selective renal effect is required or preferred. More specifically, the peptide conjugates of the invention exhibit a significant sodium-sparing and potassium-sparing aquaretic effect, which is beneficial in the treatment of edema-forming pathological conditions associated with hyponatremia and/or hypokalemia. The peptide conjugates of the invention are useful for medical treatment of humans and for veterinarian use as a diuretic during edema-forming states in livestock, such as horses and cattle. A particular advantage of the compounds of the invention is their stability in plasma compared to the hexapeptides disclosed by Dooley et al.[1]

The novel peptide conjugates of the invention are useful in the preparation of antibodies capable of specifically binding to said peptide conjugates. Antibodies raised against the peptide conjugates of the invention or fractions thereof are also disclosed.

DETAILED DESCRIPTION OF THE INVENTION

Figure 1A:
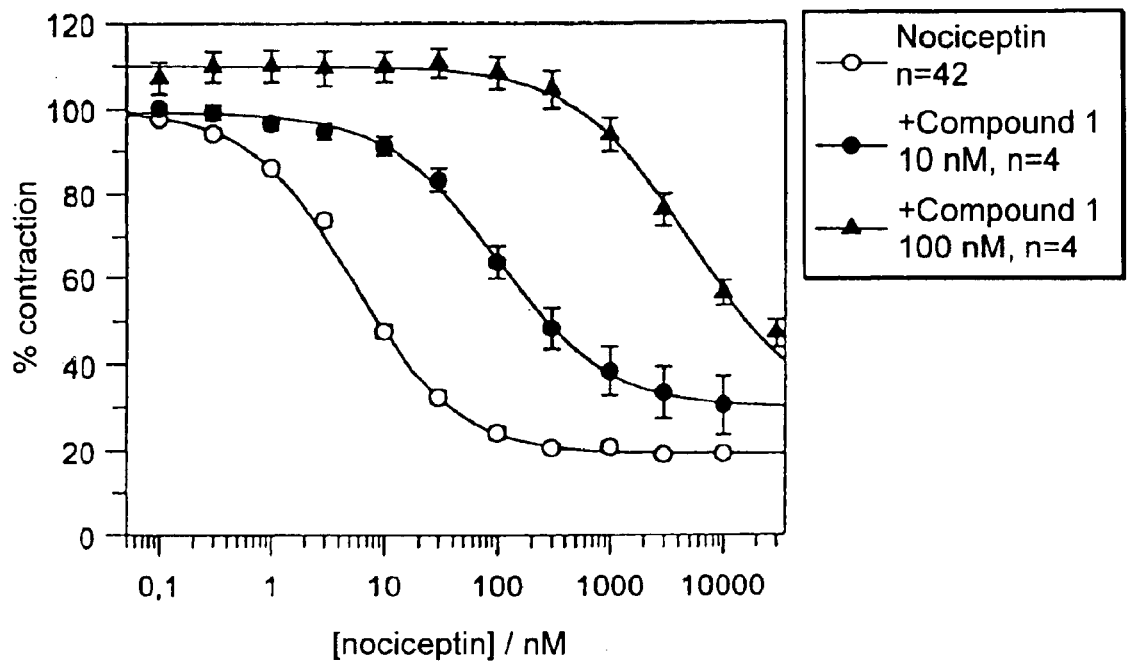
FIG. 1 shows concentration-response curves of the effects of cumulative addition of test substance (Ac-RYYRWK-NH$_2$ and Compound 1) (SEQ ID NO:1) on nociceptin-induced relaxation in the mouse vas deferens assay.

Coupling of a charged peptide moiety introduces increased polarity to or increased charge of the positively charged hexapeptide (RK)YY(RK)(WI)(RK) resulting in a peptide conjugate with enhanced stability and hydrophilicity. Said coupling is also thought to decrease the likelihood of the peptide conjugates crossing the blood-brain barrier. Besides, preliminary data suggest that C-terminal modification with K$_6$ appears to induce the α-helix structure in the hexapeptide X as determined by 1D-NMR spectra. In preferred embodiments of the invention formula II is represented by the amino acid sequence (RK)YY(RK)(WI)(RK) wherein alternative amino acid residues at positions 1, 4, 5 and 6 are shown in brackets. Alternatively, the amino acid residues R and K at positions 1, 4 and 6 may each be substituted with Orn, Dab or Dapa.

In preferred embodiments of the invention Z represents a negatively charged peptide chain of from 4 to 20 amino acid residues, Z' represents a positively charged peptide chain of from 4 to 20 amino acid residues, R$_1$ represents Ac or Tfa, and R$_2$ represents NH$_2$, or R$_2$ represents NR$_3$R$_4$ where each of R$_3$ and R$_4$ independently represents hydrogen, methyl or ethyl.

Said hexapeptide X is preferably selected form the group consisting of KYYRWR (SEQ ID NO:2), RYYRWR (SEQ ID NO:3), KWRYYR (SEQ ID NO:4), RYYRWK (SEQ ID NO:1), RYYRWK (SEQ ID NO:1) (all-D), RYYRIK (SEQ ID NO:5), RYYRIR (SEQ ID NO:6), RYYKIK (SEQ ID NO:7), RYYKIR (SEQ ID NO:8), RYYKWR (SEQ ID NO:9), and RYYKWK (SEQ ID NO:10), more preferably the group consisting of RYYRWR (SEQ ID NO:3), RYYRWK (SEQ ID NO:1), RYYRIK (SEQ ID NO:5), RYYKWR (SEQ ID NO:9), and RYYKWK (SEQ ID NO:10), more preferably said hexapeptide X is RYYRWK (SEQ ID NO:1) or KYYRWK (SEQ ID NO:11), wherein the amino acid residues are in the L-form unless otherwise specified. Furthermore, the number of amino acid residues in each of Z and Z' is preferably in the range of 4–10 or 5–10.

It is preferred that the amino acid residues of Z are selected from the group consisting of Q, T, S, P, N, E, and D having the D or L configuration, and the N-terminal amino acid of Z is selected from the group consisting of Q T, N and S having the D or L configuration and the remaining amino acid residues are selected from the group consisting of P, D and E. More specifically, Z is selected from the group consisting of, e.g. N(E)$_7$ (SEQ ID NO:12), N(E)$_6$ (SEQ ID NO:13), N(E)$_5$ (SEQ ID NO:14), N(E)$_3$ (SEQ ID NO:15), S(E)$_7$ (SEQ ID NO:16), S(E)$_6$ (SEQ ID NO:17), S(E)$_5$ (SEQ ID NO:18), S(E)$_3$ (SEQ ID NO:19), NP(E)$_4$ (SEQ ID NO:20), NP(E)$_5$ (SEQ ID NO:21), N(D)$_7$ (SEQ ID NO:22), N(D)$_6$ (SEQ ID NO:23), N(D)$_5$ (SEQ ID NO:24), N(D)$_3$ (SEQ ID NO:25), Q(E)$_7$ (SEQ ID NO:26), Q(E)$_5$ (SEQ ID NO:27), Q(E)$_3$ (SEQ ID NO:28), QN(D)$_7$ (SEQ ID NO:29), Q(D)$_6$ (SEQ ID NO:30), Q(D)$_5$ (SEQ ID NO:31), and Q(D)$_3$ (SEQ ID NO:32), preferably Z is N(E)$_5$ (SEQ ID NO:14).

It is preferred that the amino acid residues of Z' are selected from the group consisting of A, G, K, and R, preferably K, having the D or L configuration, more preferably Z' is selected from the group consisting of A(K$_4$)G, K$_5$G, AK$_5$, H$_6$, K$_{10}$, K$_8$, K$_6$, K$_5$, and K$_4$.

Examples of conjugates Z-X-Z' are N(E)$_5$RYYRWKK$_6$ (SEQ ID NO:33), N(E)$_5$RYYRWK (SEQ ID NO:34), RYYRWKK$_6$ (SEQ ID NO:35), N(E)$_5$RYYRWRK$_6$ (SEQ ID NO:36), N(E)$_5$RYYRWR (SEQ ID NO:37), RYYRWK$_6$ (SEQ ID NO:38), N(E)$_5$RYYRIKK$_6$ (SEQ ID NO:39), N(E)$_5$RYYRIK (SEQ ID NO:40), and RYYRIKK$_6$ (SEQ ID NO:41).

Exemplary compounds of the invention are: Ac-RYYRWKK$_6$-NH$_2$ (SEQ ID NO:35), Ac-K$_6$RYYRWK- NH$_2$ (SEQ ID NO:42), N(E)$_5$RYYRWKK$_6$-NH$_2$ (SEQ ID NO:35), and salts, preferably pharmaceutically acceptable salts, hydrates, solvates and derivatives thereof including C-terminal derivatives, such as free carboxylic acid.

A further preferred embodiment of the invention is represented by the general formula III

wherein R$_1$, X, Z' and R$_2$ have the same meanings as defined above, and salts, hydrates and solvates thereof and C-terminally amidated or esterified derivatives thereof with suitable organic or inorganic acids. In a preferred peptide conjugate of formula III R$_1$ represents Ac, X represents a hexapeptide of the formula (RK)YY(RK)(WI)(RK) wherein alternative amino acid residues at positions 1, 4, 5 and 6 are shown in brackets, Z' represents K$_n$, where n is an integer selected from 5, 6 or 7, and R$_2$ represents NH$_2$. X is preferably selected from the group consisting of KYYRWK (SEQ ID NO:11), RYYRWR (SEQ ID NO:3), RYYRWK (SEQ ID NO:1), RYYRWK (all-D), KWRYYR (SEQ ID NO:4), RYYRIK (SEQ ID NO:5), RYYKWR (SEQ ID NO:9), and RYYKWK (SEQ ID NO:10). The peptide conjugates of formulae I and III are optionally further linked to a transport moiety or an affinity tag, such as H$_6$, where the linkage between the peptide conjugate and said transport moiety or affinity tag may be by any convenient covalent bond. Said transport moiety is preferably selected from the group consisting of a HIV tat peptide residues 49–57, HIV tat peptide residues 49–56, the tat sequence YGRKKRRQRRR (SEQ ID NO:43), a polyarginine peptide having from 6 to 20 residues, such as R$_6$, and transducing peptide sequences, such as the following peptide sequences: YARKARRQARR (SEQ ID NO:44), YARAAARQARA (SEQ ID NO:45), YARAARRAARR (SEQ ID NO:46), YARAARRAARA (SEQ ID NO:47), ARRRRRRRRR (SEQ ID NO:48), and YAAARRRRRRR (SEQ ID NO:49), which are disclosed in WO 99/29721 and in U.S. Pat. No. 6,221,355 (seq. id. nos. 3–8) the disclosures of which are incorporated by reference.

The peptide sequence of a compound of formulae I and III is optionally in the all-D form, the retro form or the retro all-D form, where the all-D form is more preferred. Optionally, the X sequence of formulae I and III is an all-D form, a retro form, or a retro all-D form of the peptide sequence of formula II or the hexapeptide (RK)YY(RK)(WI)(RK) as defined above, respectively.

Exemplary compounds of the invention are shown in Table 1 below:

```
Compound 1   Ac-RYYRWKKKKKKK-NH2       (SEQ ID NO:38)
Compound 2   Ac-KKKKKKRYYRWK-NH2       (SEQ ID NO:42)
Compound 3   H-NEEEEERYYRWKKKKKKK-NH2  (SEQ ID NO:34)
Compound 4   Ac-RYNRWKKKKKKK-NH2       (SEQ ID NO:50)
Compound 5   Ac-KKKKKKKWRYYN-NH2       (SEQ ID NO:51)
Compound 6   Ac-KKKKKKKWRYYR-NH2       (SEQ ID NO:52)
Compound 7   Ac-KKKKKKKWRYYR-NH2       (SEQ ID NO:52)
             (all D)
Compound 8   Ac-RYYRWKKKKKKK-NH2       (SEQ ID NO:35)
             (all D)
Compound 9   Ac-KYYRWKKKKKKK-NH2       (SEQ ID NO:53)
Compound 10  Ac-RYYRIKKKKKKK-NH2       (SEQ ID NO:41)
Compound 11  Ac-RYYRWKAKKKKK-NH2       (SEQ ID NO:54)
Compound 12  Ac-RYYRWKKKKKK-NH2        (SEQ ID NO:55)
Compound 13  Ac-RYYRWKKKKKKKC-NH2      (SEQ ID NO:56)
Compound 14  Tfa-RYYRWKKKKKKK-NH2      (SEQ ID NO:35)
``` and salts, hydrates, solvates and C-terminal derivatives thereof, such as the free carboxylic acid.

Other preferred compounds are
Ac-KWRYYNKKKKKK-NH$_2$ (SEQ ID NO:57)
Ac-KWRYYRKKKKKK-NH$_2$ (SEQ ID NO:58) and
Ac-KWRYYRKKKKKK-NH$_2$ (SEQ ID NO: 58)(all D) and salts, hydrates, solvates and C-terminal derivatives thereof, such as the free carboxylic acid.

Examples of acid addition salts with an organic and an inorganic acid of compounds of the invention are Compound 1A Ac-RYYRWKKKKKKK-NH$_2$ (SEQ ID NO:35)×9CH$_3$COOH and Compound 1C Ac-RYYRWKKKKKKK-NH$_2$×9HCl. (SEQ ID NO:35)

The peptide conjugates of the invention are preferably prepared using the method of synthesis disclosed in WO 98/11125 the disclosure of which is incorporated by reference, and preferably using a method as described in Example 15 therein. Said methods of synthesis will result in a primary peptide product having a trifluoroacetate counterion and which may be suitable for the preparation of a medicament. In many instances, however, it may be advantageous to perform a counter ion exchange from trifluoroacetate to a pharmaceutically acceptable or preferred anion, such as acetate. This may be effected by ion exchange chromatography. Alternatively, the primary peptide product may be repeatedly freeze dried and dissolved in diluted hydrochloric acid to obtain the purified hydrochloride.

Also included in the present invention is the use of a peptide conjugate of formula I or III or an epitopic fragment thereof comprising a part or all of the X sequence of formula II or the formula (RK)YY(RK)(WI)(RK) and/or a part or all of the Z sequence or the Z' sequence preferably coupled to a carrier through a terminal cysteinyl residue for raising antibodies capable of specifically binding to said peptide conjugates or said X sequence. The terminal Cys residue is optionally obtained through the substitution with a Cys residue of one of the terminal aminoacid residues of said peptide conjugate or said epitopic frament thereof, or said peptide conjugate or said epitopic fragment thereof comprises a further Cys residue at one of its termini. Examples of peptide fragments having a terminal C useful for raising antibodies capable of specifically binding to the peptide conjugates of the invention are RYYRWKC (SEQ ID NO:59), KYYRWKC (SEQ ID NO:60), CWKKKKKKK (SEQ ID NO:61), CKKKKKK (SEQ ID NO:62), and CWKKKKKK (SEQ ID NO:63). In addition, peptide fragments having a considerable sequence homology to the peptide conjugates of the invention can be used for raising antibodies capable of specifically binding to the peptide conjugates of the invention. Examples are CAPPSKKKKKK (SEQ ID NO:64), CAAPKKKKKK (SEQ ID NO:65), CPPSKKKKKK (SEQ ID NO:66), etc. Optionally, each of the foregoing peptide conjugates having a Cys terminus can have at least one amino acid in the D form.

As will be discussed in more detail below, the novel peptide conjugates can be administered as a sole active agent or in combination with one or more medicaments such as those specifically provided below.

Throughout the description and claims the one letter code for natural amino acids is used as well as the three letter code for natural amino acids and generally accepted three letter codes for other α-amino acids, such as Ornithine (Orn), 2,4-Diaminobutanoic acid (Dab) and 2,3-Diaminopropanoic acid (Dapa). Where the L or D form has not been specified it is to be understood that the amino acid in question has the natural L form, cf. Pure & Appl. Chem. Vol. 56(5)

pp595–624 (1984). Where nothing is specified it is to be understood that the C-terminal amino acid of a compound of the invention exists as the free carboxylic acid, this may also be specified as "—OH". Cf. Biochem. J., 1984, 219, 345–373; Eur. J. Biochem., 1984, 138, 9–37; 1985, 152, 1; 1993, 213, 2; Internat. J. Pept. Prot. Res., 1984, 24, following p 84; J. Biol. Chem., 1985, 260, 14–42; Pure Appl. Chem., 1984, 56, 595–624; Amino Acids and Peptides, 1985, 16, 387–410; Biochemical Nomenclature and Related Documents, 2nd edition, Portland Press, 1992, pages 39–69; Copyright IUBMB and IUPAC. The term "retro form" of a peptide conjugate of formulae I or III refers to a peptide having the reversed aminoacid sequence of formulae I or III. The term "all-D form" of a peptide conjugate of formulae I or III refers to a peptide wherein all aminoacid units are in the D-form. The term "retro all-D form" of a peptide conjugate of formulae I or III refers to a peptide having the reversed aminoacid sequence of formulae I or III and wherein all aminoacid units are in the D-form (retro-inverse form). Optionally, in a peptide conjugate of the invention the sequence defined by formula II or the formula (RK)YY(RK)(WI)(RK) is in the all-D form, the retro form or the retro all-D form. D-aminoacids are unnatural aminoacids which are stable in a protease rich environment. Thus, a useful way of stabilising the peptide conjugates of the invention against proteolytic degradation is to substitute L-aminoacids with corresponding D-aminoacids. The term "epitopic fragment" refers to a truncated or shortened section of a peptide sequence having, e.g., 5–8 aminoacid units and is capable of eliciting an antigen response.

The term "alkyl" refers to univalent groups derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively. "Alkyl" refers to any alkyl group, and includes C(1–6)alkyl, such as methyl, ethyl, propyl, iso-propyl, butyl, pentyl and hexyl and all possible isomers thereof. By "lower alkyl" is meant C(1–6)alkyl, preferably C(1–4)alkyl, more preferably, methyl and ethyl.

The term "C(1–6)alkoxy" refers to an ester group of the formula R—O— wherein R represents C(1–6)alkyl. The term "aryloxy" refers to an ester group of the formula R—O— wherein R represents phenyl or naphthyl optionally substituted with a lower alkyl group.

The term "acyl" as used herein include acyl radicals which are formally derived from oxoacids $R_kE(=O)_l(OH)_m$ (l not equal to 0) by removal of a hydroxyl cation $HO^+$, a hydroxyl radical $HO^-$ or a hydroxyl anion $HO^-$, respectively, and replacement analogues of such intermediates. Acyl radicals can formally be represented by canonical forms having an unpaired electron or a positive charge on the acid-generating element of the oxoacid. Acyl radicals, e.g. $RC(=O)$, $RS(=O)_2$.

The term "acylated" as used herein indicates the compound in question carries an acyl group. An acyl group is formed by removing one or more hydroxy groups from an oxoacid, such as a carboxylic acid, that has the general structure $R_kE(=O)_l(OH)_m$ (l not equal to 0), and replacement analogues of such acyl groups. E.g.$CH_3C(=O)$—, $CH_3C(=NR)$—, $CH_3C(=S)$—, $PhS(=O)_2$—, $HP(N)$—. In organic chemistry an unspecified acyl group is commonly a carboxylic acyl group. Cf. International Union of Pure and Applied Chemistry, Recommendations on Organic & Biochemical Nomenclature, Symbols & Terminology etc. IUPAC Recommendations 1994. "Ac" indicates an acetyl group and "Tfa" indicates a trifluoroacetyl group.

The term "peptide conjugate" as used herein indicates a fusion between at least two peptide sequences via a peptidic bond or an equivalent bioisosteric bond, such as the peptide bond mimetics described in Table 1 in Tayar et al., Amino Acids (1995) 8:125–139.

The term "transport moiety" as used herein indicates a chemical entity that acts in escorting molecules such as polypeptides across biological membranes. The transport polymers disclosed in WO 98/52612 are all incorporated by reference. Peptide conjugates of the invention are linked via a covalent bond to said transport moiety. The term "HIV tat peptide residues 49–57" refers to a transport moiety having the sequence RKKRRQRRR (SEQ ID NO:67) as disclosed in WO 91/09958.

"Agonist" refers to an endogenous substance or a drug that can interact with a receptor and initiate a physiological or a pharmacological response characteristic of that receptor (contraction, relaxation, secretion, enzyme activation, etc.).

"Antagonist" refers to a drug or a compound that opposes the physiological effects of another. At the receptor level, it is a chemical entity that opposes the receptor-associated responses normally induced by another bioactive agent.

"Partial agonist" refers to an agonist which is unable to induce maximal activation of a receptor population, regardless of the amount of drug applied (See also Intrinsic activity). A "partial agonist" may also be termed "agonist with intermediate intrinsic efficacy" in a given tissue. Moreover, a partial agonist may antagonize the effect of a full agonist that acts on the same receptor.

"Receptor" refers to a molecule or a polymeric structure in or on a cell that specifically recognizes and binds a compound acting as a molecular messenger (neurotransmitter, hormone, lymphokine, lectin, drug, etc.).

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques. Examples of such pharmaceutically acceptable salts include, but are not limited to, inorganic and organic acid addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well. "Pharmaceutically acceptable anions" as used herein includes the group consisting of $CH_3COO^-$, $CF_3COO^-$, $Cl^-$, $SO_3^{2-}$, maleate and oleate.

The term "peripheral administration" includes all administration forms that exclude delivery of the active substance directly into the central nervous system. "Central administration" as used herein means an administration directly into the central nervous system, such as intracerebroventricular administration (i.c.v. administration).

The term "hyponatremia" as used herein includes but is not necessarily limited to the following medical conditions:
Pseudohyponatremia characterised by
   Normal plasma osmolality associated with, e.g., hyperlipidemia, hyperproteinemia or posttransurethral resection of prostate/bladder tumor, and
   increased plasma osmolality associated with, e.g., hyperglycemia and mannitol;

Hypoosmolal hyponatremia characterised by
  Primary Na+ loss (secondary water gain) associated with, e.g., integumentary loss: sweating, burns; gastrointestinal loss: vomiting, tube drainage, fistula, obstruction, diarrhea; renal loss: diuretics, osmotic diuresis, hypoaldosteronism, salt-wasting nephropathy, postobstructive diuresis, nonoligouric acute tubular necrosis;
  Primary water gain (secondary Na+ loss) associated with, e.g. primary polydipsia; decreased solute intake (e.g., beer potomania); AVP (vasopressin) release due to pain, nausea, drugs; syndrome of inappropriate AVP secretion; glucocorticoid deficiency; hypothyroidism and chronic renal insufficiency; and
  Primary Na+ gain (exceeded by secondary water gain) associated with, e.g. heart failure, hepatic cirrhosis and nephrotic syndrome.

Congestive Heart Failure (CHF)

Congestive heart failure (CHF) is the pathophysiological state in which an abnormality in cardiac function is responsible for the failure of the heart to pump blood at a rate commensurate with the requirements of the metabolizing tissues. Regardless of the underlying cause of CHF (e.g., ischemic heart disease, arterial hypertension, dilated cardiomyopathy, valvular disease, anemia etc.), the major clinical manifestation of heart failure is dyspnea which appears with less strenuous activity as the disease progresses. According to the New York Heart Association (NYHA) functional classification, the CHF patients may be classified into one of four classes (class I, class II, class III, class IV). This functional classification is used worldwide and has a strong association with mortality, which is independent of left ventricular ejection fraction.

Congestive heart failure is characterized by a complex series of neurohumoral adjustments. The major mechanisms are activation of the sympathetic nervous system, stimulation of the renin-angiotensin-aldosterone axis, and stimulation of vasopressin release. These influences elevate systemic vascular resistance and enhance sodium and water retention, while potassium excretion is increased due to hyperaldosteronism. Due to activation of water retaining mechanisms patients with end-stage CHF have a reduced capacity to excrete water, and unless water intake is restricted, these patients are at great risk of developing dilutional hyponatremia.

Current Therapy of CHF

The purpose of medical treatment is to relieve the patients from debilitating symptoms without compromising the myocardial function too severely. During progression of CHF, the medical treatment is intensified by addition of drugs with different sites of action. The current treatment of heart failure can be divided into three categories: (1) Reduction of cardiac workload including preload and afterload; (2) control of excessive retention of water and salt; (3) enhancement of myocardial contractility. NYHA class IV patients are usually in treatment with maximal doses of vasodilators, such as ACE inhibitors, hydralazine, alpha-adrenergic inhibitors, and nitrates. However, pulmonary congestion due to water and salt retention is still a major problem for these patients. Despite the intensive medical therapy with drugs from all classes, the mortality and morbidity is still very high in patients with CHF.

Patients in severe heart failure (NYHA class III–IV) usually require a combination of at least two different diuretics with different tubular sites of action. The most commonly used is a combination of a loop diuretic (e.g., furosemide, bumetanide) and a thiazide diuretic (e.g., chlorothiazide, bendroflumethiazide). High doses of this combination are the most effective therapy for producing natriuresis (maximal efficacy is about 30% of filtered load for loop diuretics and about 10% for thiazides). However, blockade of the thiazide-sensitive sodium reabsorption in the distal convoluted tubules (i.e., the diluting segment) may produce hypertonic urine and contribute to dilutional hyponatremia. Hyperaldosteronism and the associated increase in delivery of sodium to the collecting ducts, stimulates sodium-potassium exchange in the collecting ducts resulting in kaliuresis. Thus, combination therapy with loop diuretics and thiazides is the most common cause for both hyponatremia and hypokalemia in heart failure patients. Potassium-sparing diuretics (e.g., spironolactone, amiloride) may be used in combination with thiazides or loop diuretics, but the poor maximal efficacy (max. 3% of filtered water) of these compounds makes these drugs weak diuretics.

In addition, due to hyperaldosteronism, patients with end-stage CHF are at great risk of developing hypokalemia.

When symptoms such as dyspnea at rest, orthopnea and paroxysmal nocturnal dyspnea persist despite maximal medical treatment with loop diuretics (=loop-diuretic resistant CHF or refractory CHF), additional diuretic therapy is necessary to avoid life threatening pulmonary congestion. Thiazides are often added as the first drug of choice when the therapeutic effect of loop diuretics fails. The combination of loop diuretics+thiazides produce an effective natriuresis, however, inhibition of sodium reabsorption in the thiazide-sensitive diluting segment of the nephron, often results in hypertonic urine, which may result in serious electrolyte disturbances. Thus, combination of loop diuretics and thiazides is the most common cause of hypokalemia and hyponatriemia in patients with NYHA class IV heart failure [3].

Hypokalemia is a major predisposing mechanism for the development of arrhythmias and the prognosis of CHF is poor when serum potassium levels fall below 3.3 mM. Furthermore, in CHF patients treated with digoxin, hypokalemia is the most common precipitating cause of digitalis intoxication, which is a serious and potentially fatal complication.

In patients with severe heart failure, combination treatment with loop diuretics and thiazides often produces hypotonic hyponatremia as a consequence of increased sodium losses and impaired water excretion. If the hyponatremia develops faster than the brain can adapt, symptoms of cerebral edema develop (e.g., headache, nausea, vomiting, weakness, incoordination, tremors, delirium, and ultimately seizures and coma). Deaths occur when the serum level of sodium (S—Na) falls below 120 mM at a rate that exceeds 1 mmol/l/hr. When the hyponatremia develops more gradually, the symptoms are more subtle, vague and non-specific and they tend to occur at even lower S—Na levels. Typically symptoms include personality changes (depression, non-cooperation, confusion), anorexia, nausea, muscular weakness, and cramps. When S—Na<120 mM gait disturbances, stupor, and seizures may occur.

Class IV represents the group of patients with end-stage heart failure. Among the characteristic clinical manifestations, the dyspnea at rest is the most striking symptom. As heart failure advances dyspnea appears with progressively less strenuous activity, however, during end-stage heart failure, dyspnea even in the recumbent position (orthopnea) is a common finding. The patients have engorged pulmonary vessels and interstitial pulmonary edema, which is often evident on radiological examination. Patients with orthopnea must elevate their heads to relieve the pulmonary congestion, and they are frequently awake during night with severe attacks of coughing and the sensation of breathlessness (nocturnal dyspnea). This condition is quite frightening and the anxiety often worsens the symptoms of heart failure.

Along with pulmonary congestion in class IV patients, the reduced cardiac function is associated with congestion of the liver and the portal venous system, which produces anorexia, nausea and abdominal pain. Patients belonging to class IV have an extremely high 1-year mortality (30–80%). The major causes of death are sudden death (40%) and worsening of the congestive heart failure (40%). Among the factors that are associated with poor prognosis is low ejection fraction (<25%), reduced oxygen uptake, reduced serum sodium concentration (<133 mM), and reduced serum potassium concentration (<3 mM)[3]. The peptide conjugates of the invention exhibit an advantageous pharmacological profile suggesting an ability to alleviate pulmonary congestion, decrease pre- and afterload, increase cardiac output and oxygen uptake, and prevent hyponatremia and hypokalemia.

When cardiac output is reduced a series of compensatory adjustments occurs that ultimately results in the abnormal accumulation of fluid. In CHF patients with NYHA Class I through III, the abnormal fluid accumulation and the accompanying expansion of blood volume constitutes an important compensatory mechanism that tends to maintain cardiac output and perfusion to vital organs. However, in the terminal stage of heart failure (NYHA class IV) the cardiac ventricles operate on a depressed and flattened function curve, and in terminal heart failure, the patient end up on the descending part of the Starling volume-cardiac output curve. Thus, these patients need effective diuretic therapy in order to control blood volume and prevent life threatening pulmonary edema. The advantageous effects of the peptide conjugates of the invention in heart failure, such as loop diuretic-resistant refractory heart failure, are to decrease blood volume and pulmonary congestion. If the patient is on the flattened part of the curve, cardiac output decreases slightly, and if the patient is on the descending part of the curve cardiac output may increase[3].

Having a unique pharmacological profile as a potassium- and sodium-sparing aquaretic, the peptide conjugates of the invention, such as Compound 1, represent the ideal candidate drugs for the treatment of CHF symptoms in patients with refractory heart failure who no longer respond sufficiently to high doses of loop diuretics. In these patients, the novel peptide conjugates as an add-on or combination therapy to loop diuretics may promote an effective diuresis without the accelerated sodium and potassium losses seen with other diuretics. The same unique pharmacological profile will also present an advantage in the treatment of hyponatremia, renal disease, and edema associated with nephrotic syndrome and liver cirrhosis.

Pharmacology

Mouse Vas Deferens Assay

The compounds of the present invention are pharmacologically active, e.g. as nociceptin agonists or partial agonists, and a useful method of showing activity is described by Hughes J., Kosterlitz H. W., Leslie F. M.: Effect of morphine on adrenergic transmission in the mouse vas deferens. Assessment of agonist and antagonist potencies of narcotic analgesics [4]. The isolated electrically stimulated mouse vas deferens preparation has been widely used to evaluate the functional pharmacological actions of opioid agonists and antagonists in vitro [5]. The mouse vas deferens possesses all three opioid receptor types and subsequent studies have described that the mouse vas deferens assay is also sensitive to nociceptin [6].

The vas deferens from male NMRI albino mice weighing 30–40 g were placed in a SCHULER organ bath Type 809, Hugo Sachs Elektronik, Germany, and perfused with a 37° C., modified Krebs solution (NaCl 6,9 g/L, KCl 0,35 g/L, $KH_2PO_4$ 0,16 g/L, $NaHCO_3$ 2,1 g/L, Glucose $H_2O$ 2,0 g/L, $CaCl_2$ 2,52 mL/L). The solution was gassed with carbogen (95% $O_2$ and 5% $CO_2$) throughout the experiment. The tissue was electrically stimulated through two silver electrodes directly in the organ bath using a HSE Stimulator I Type 215. Stimulation of the tissue was performed by applying a supramaximal voltage (15 Volts) in trains of 10 square pulses every 60 s, each of 1 ms duration with a frequency of 100 ms. Concentration-response curves were performed by adding test substances that relax mouse vas deferens smooth muscles cumulatively to the organ baths. The test substances used in the assay were nociceptin in an isotonic saline solution, Compound 1 (as the trifluoroacetate in an isotonic saline solution), Compound 2 (as the trifluoroacetate in an isotonic saline solution), and the hexapeptide Ac-RYYRWK-$NH_2$ (SEQ ID NO:1) (as the trifluoroacetate in an isotonic saline solution). The peptide conjugates of the present invention are biologically active in the mouse vas deferens (MVD) assay, but the compounds inhibit electrically-induced contraction of the mouse vas deferens with varying potency: nociceptin>Compound 1=Compound 2>>Ac-RYYRWK-$NH_2$ (SEQ ID NO:1) (data not shown).

Figure 1B:
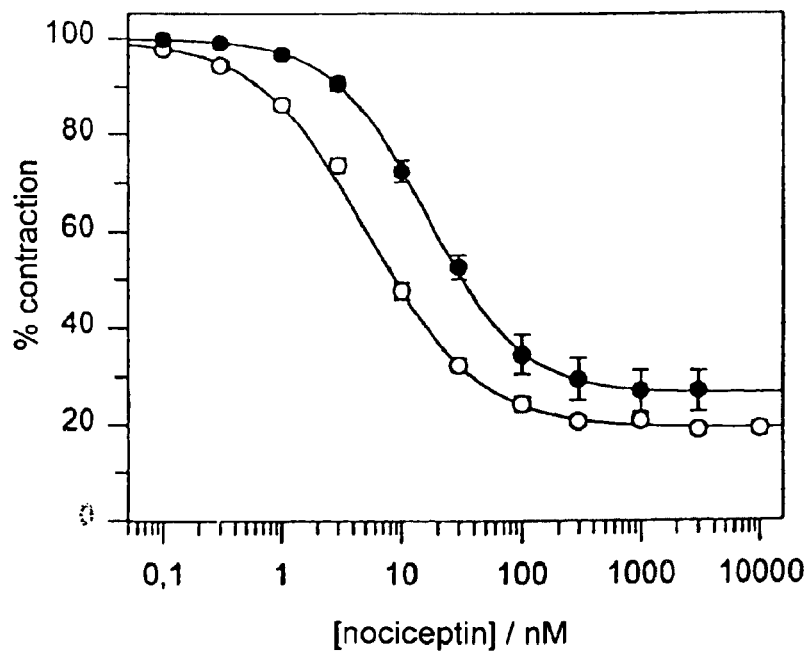

The effects of Ac-RYYRWK-$NH_2$ (SEQ ID NO:1 and Compound 1 on nociceptin-induced relaxation in the mouse vas deferens assay were also tested. Results from these experiments are shown in FIG. 1. These data demonstrate that both the partial agonist Ac-RYYRWK-$NH_2$[1] and the peptide conjugate referred to as Compound 1 inhibit nociceptin-induced smooth muscle relaxation. Using the Schild equation [7], the $pA_2$ values which indicates affinity of a compound as an antagonist were calculated. These results are presented in Table 2:

TABLE 2

|  | Ac-RYYRWK-$NH_2$ (SEQ ID NO: 1) | Compound 1 |
| --- | --- | --- |
| $pA_2$ value (number of experiments) | 7.8 (n = 4) | 9.5 (n = 4) |

These data demonstrate that Compound 1 is about 50-fold more potent as an antagonist on the nociceptin-induced smooth muscle relaxation in the MVD assay than the unconjugated hexapeptide Ac-RYYRWK-$NH_2$. (SEQ ID NO:1)

In Vivo Studies

Previous studies have demonstrated that nociceptin produces a marked increase in urine flow rate and decrease in urinary sodium excretion (i.e., an aquaretic response) when administered centrally (intracerebro-ventricularly, i.c.v.) or as an i.v. infusion in conscious rats [8–10]. In the conscious rat model, the animal is chronically instrumented with catheters in the urinary bladder, the femoral artery, and the femoral vein. The animal receives a continuous i.v. infusion with isotonic saline, 50 μl/min. Urine is collected in vials in consequtive urine collection periods of 10 min each. After two control periods, the test compound is administered and fractionated urine collections (10 min periods) are continued for at least two hours. Urinary concentrations of sodium and potassium are determined by flame photometry (Instrumentation Laboratory 943) using caesium as internal standard.

The diuretic effect of the peptide conjugates of the invention has been tested in conscious rats, where Compound 1 elicits a powerful and sustained diuretic response. Cardiovascular and renal responses produced by i.v. infusion of nociceptin (Phoenix Pharmaceuticals) and Compound 1 have been studied in conscious Sprague Dawley rats. The results are shown in FIGS. 2 to 8 wherein HR is heart rate, MAP is mean arterial pressure, V is urine flow rate, $U_{Na}V$ is urinary excretion rate of sodium, RSNA is renal sympathetic nerve activity expressed as % of the control level, $C_{osm}$ is the osmolar clearance, and $C_{H2O}$ is free water clearance.

Figure 2:
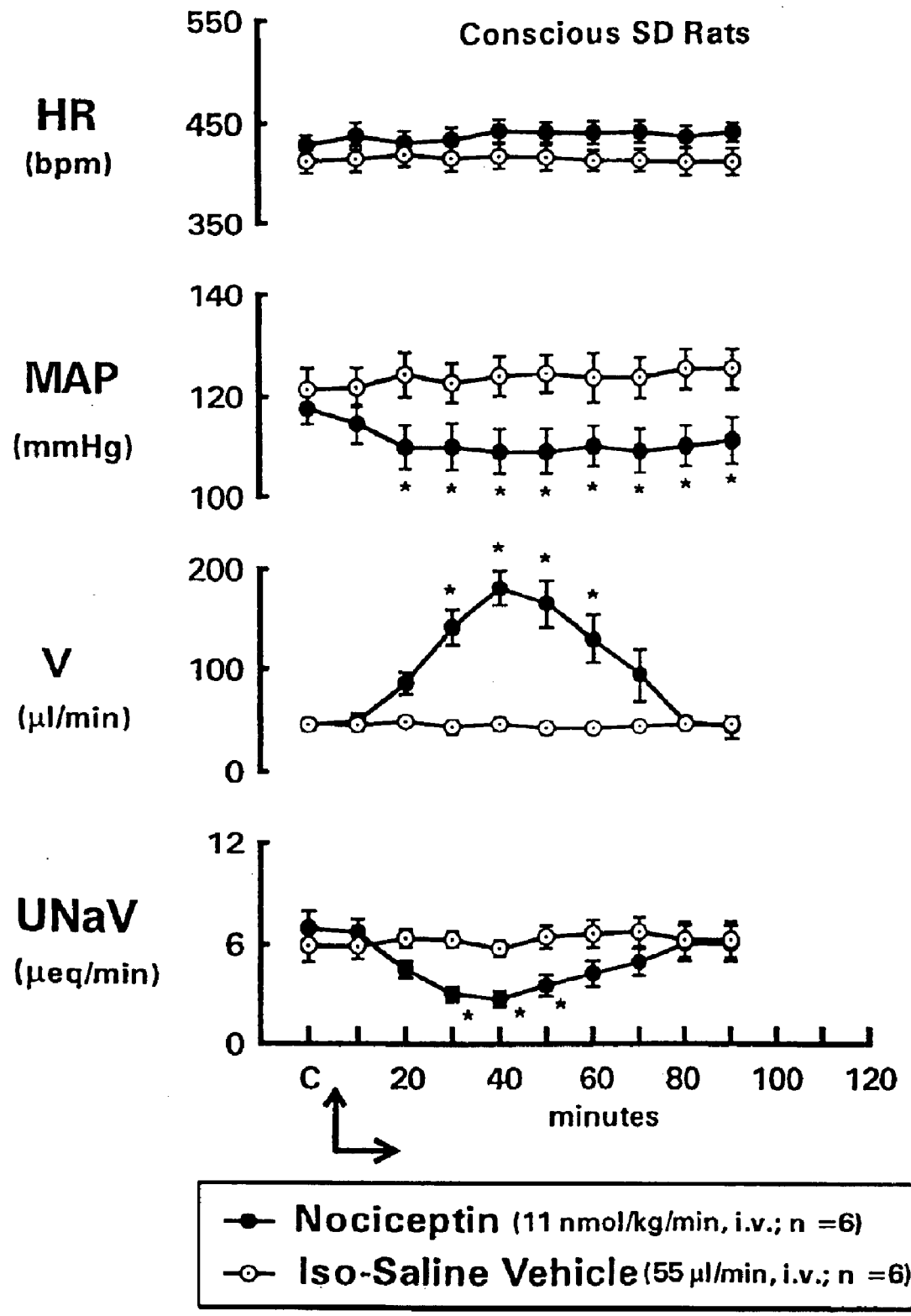
FIG. 2 shows cardiovascular and renal responses of i.v. infused nociceptin (11 nmol/kg/min); HR is heart rate (beats per minute, bpm), MAP is mean arterial pressure (mmHg), V is urine flow rate (µL/min), and UNaV is urinary excretion rate of sodium (µeq/min).

FIG. 2 shows the typical cardiovascular and renal responses of i.v. infused nociceptin (11 nmol/kg/min). Nociceptin significantly decreases MAP possibly due to relaxation of arterial smooth muscle [11].

Figure 3:
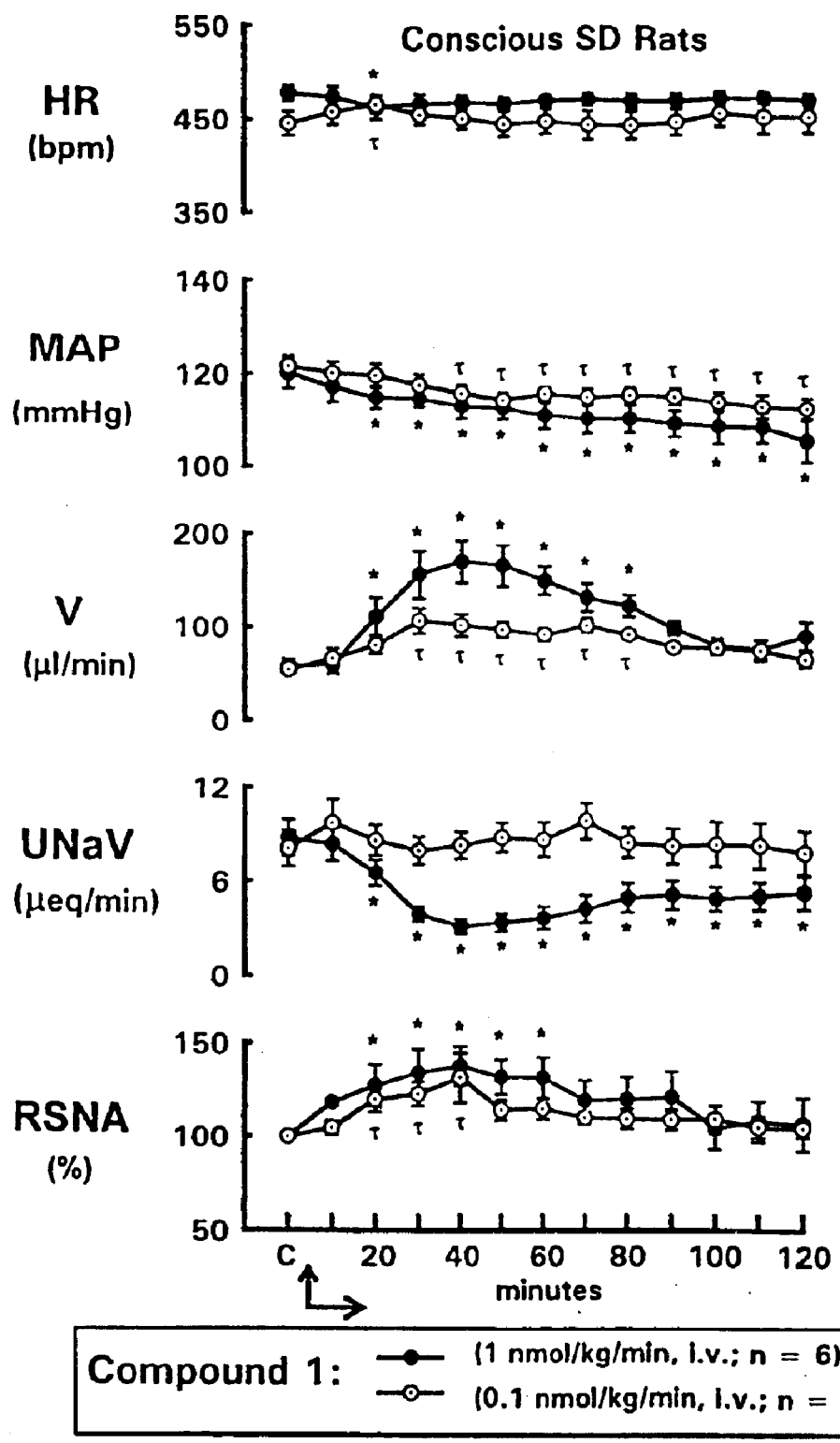
FIG. 3 shows cardiovascular and renal responses of i.v. infused Compound 1 (1 and 0.1 nmol/kg/min) as well as renal sympathetic nerve activity as percent of the control level (RNSA, %).

FIG. 3 shows significant diuretic (V µl/min) and antinatriuretic responses ($U_{Na}V$ µeq/min) of i.v. infused Compound 1 (1 and 0.1 nmol/kg/min). Similar to i.v. nociceptin, Compound 1 produced a slight, but significant reduction in MAP with little effect on HR. All rats infused with compound 1 showed no signs of increased appetite, sedation, or behavioral changes normally associated with nociceptin treatment.

Figure 4:
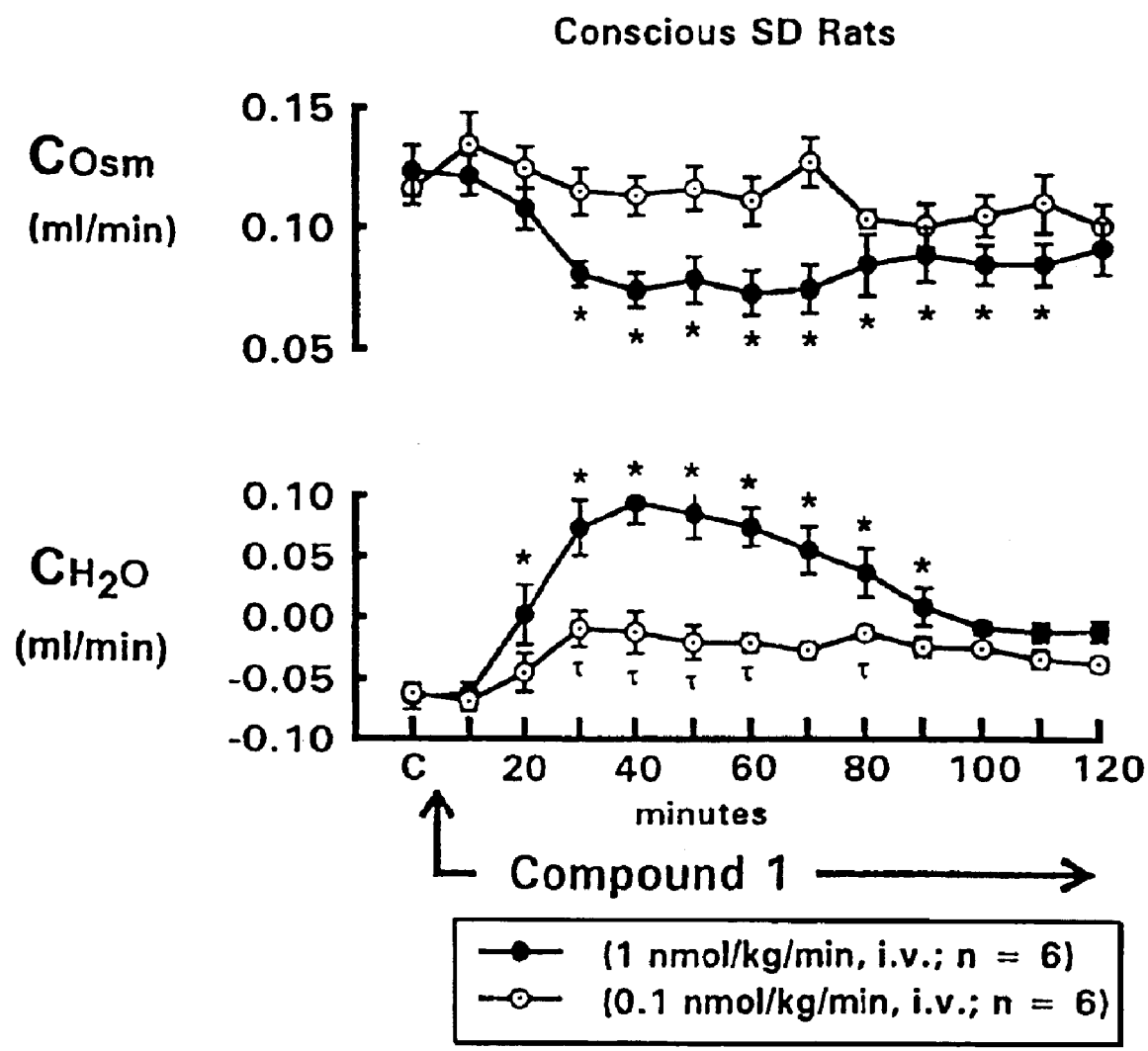
FIG. 4 shows the decrease in osmolar clearance (COsm) and the increase in free water clearance (CH$_2$O) observed during i.v. infusion of Compound 1 (1 and 0.1 nmol/kg/min).

FIG. 4 shows the decrease in osmolar clearance and the increase in free water clearance observed during i.v. infusion of Compound 1 (1 and 0.1 nmol/kg/min).

Figure 5:
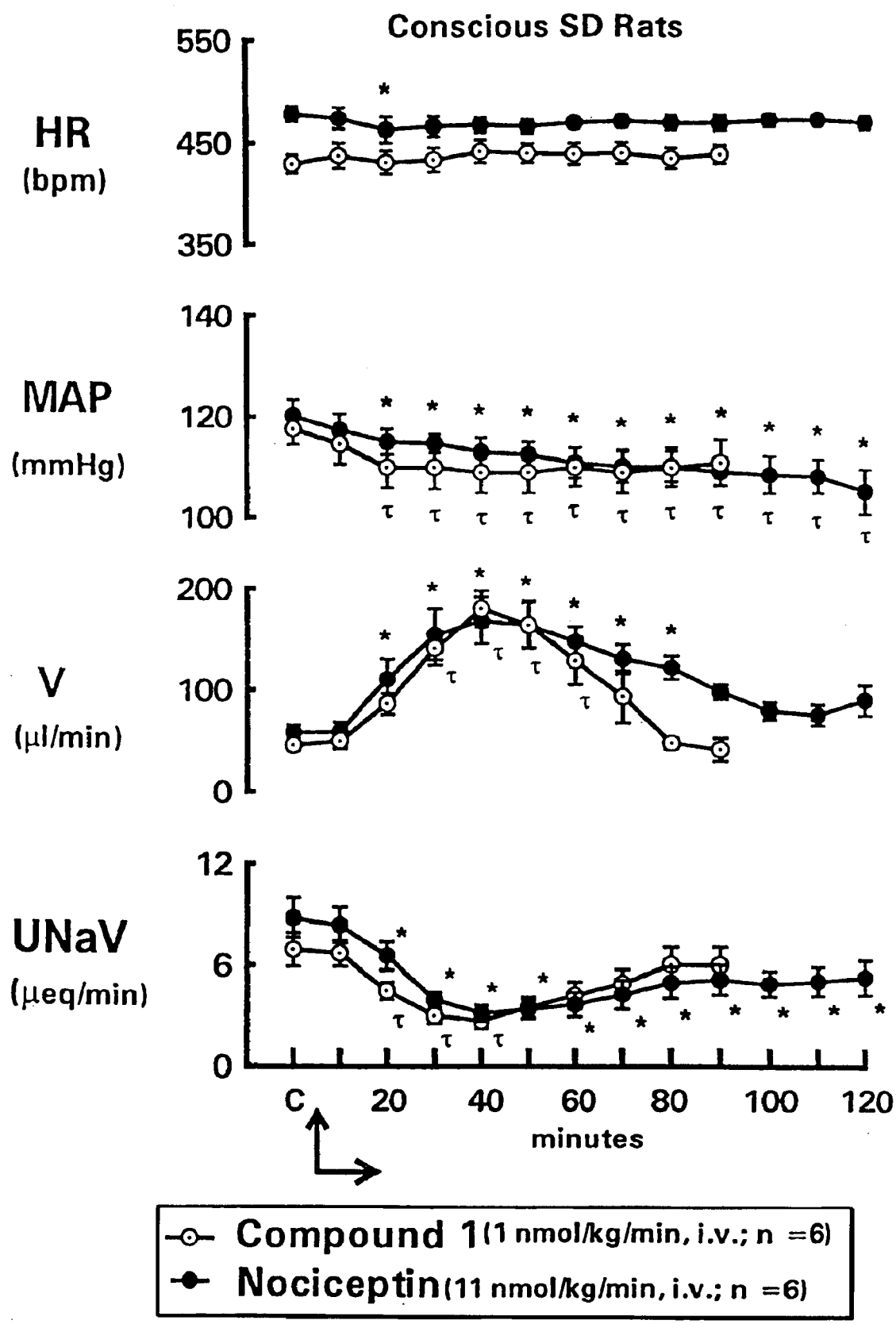
FIG. 5 illustrates the similar magnitude of changes in cardiovascular and renal responses (V and U$_{Na}$V) elicited by i.v. infusion of 1 nmol/kg/min of Compound 1 and 11 nmol/kg/min of nociceptin.

FIG. 5 illustrates the similar magnitude of changes in V and $U_{Na}V$ elicited by i.v. infusion of 1 nmol/kg/min Compound 1 and 11 nmol/kg/min of nociceptin.

Figure 6:
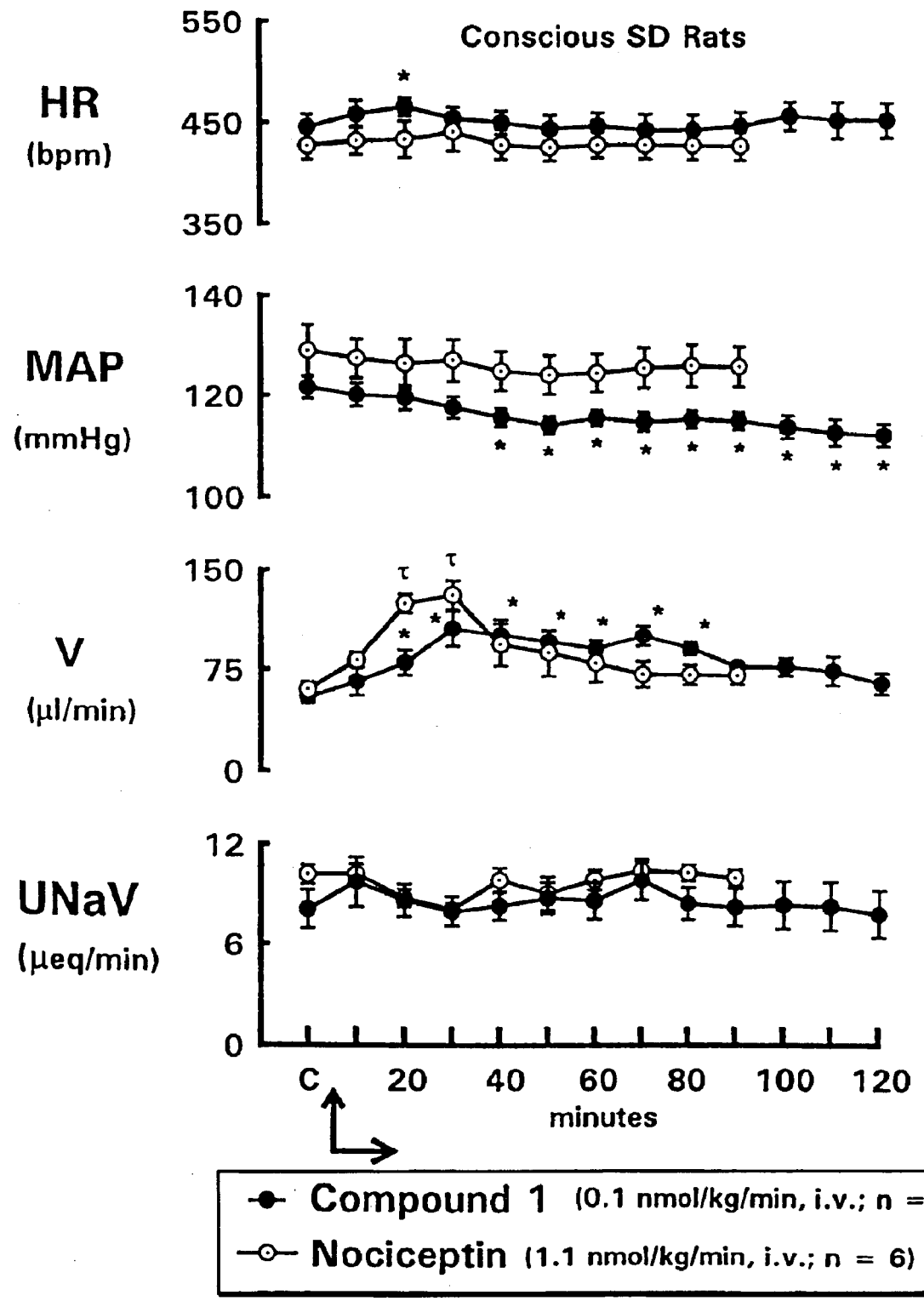
FIG. 6 illustrates the similar magnitude of changes in cardiovascular and renal responses (V and U$_{Na}$V) elicited by i.v. infusion of 0.1 nmol/kg/min Compound 1 and 1.1 nmol/kg/min of nociceptin.
Figure 7A:
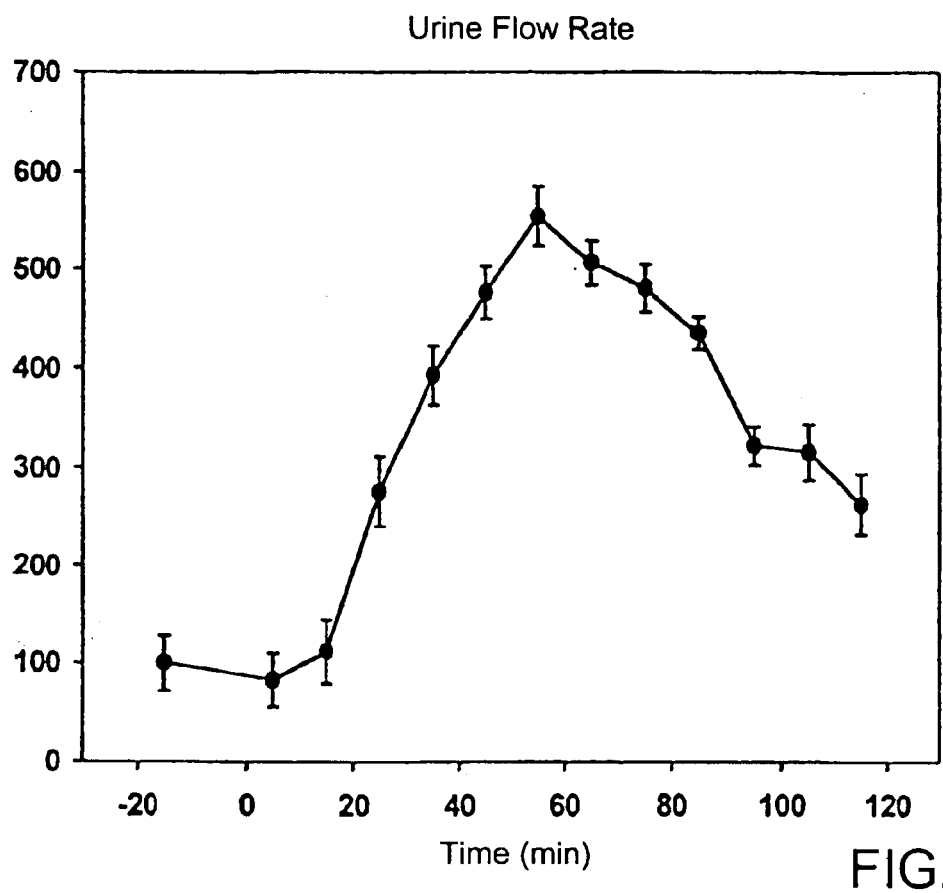
FIG. 7 is an illustration of the relationship between changes in urine flow rate, sodium and potassium excretion after i.v. administration of Compound 1, 65 nmol/kg i.v. (arrow) in normal rats. Data are expressed relative (percent) to the level prior to i.v. administration of Compound 1.
Figure 7B:
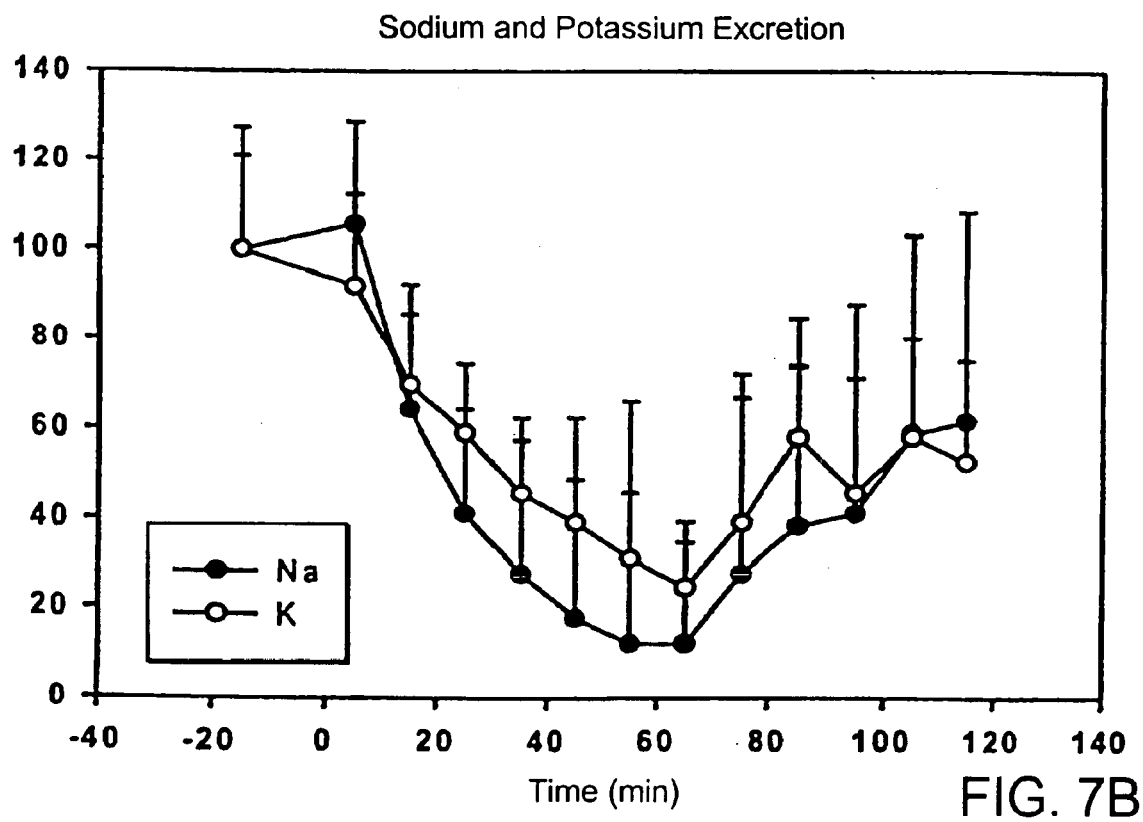
Figure 8B:
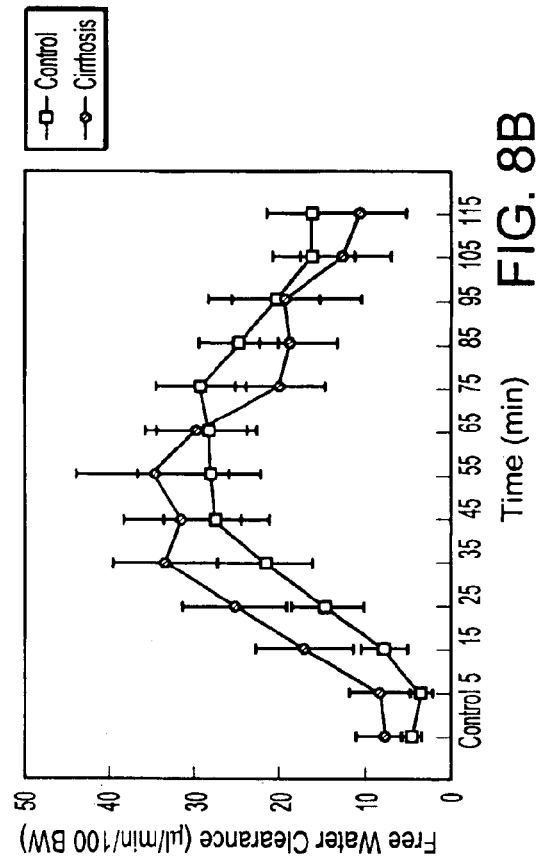
FIG. 8 illustrates changes in urine flow rate, free water clearance, fractional potassium excretion, and fractional sodium excretion after i.v. administration of Compound 1, 65 nmol/kg i.v. in normal rats and cirrhotic rats.
Figure 8D:
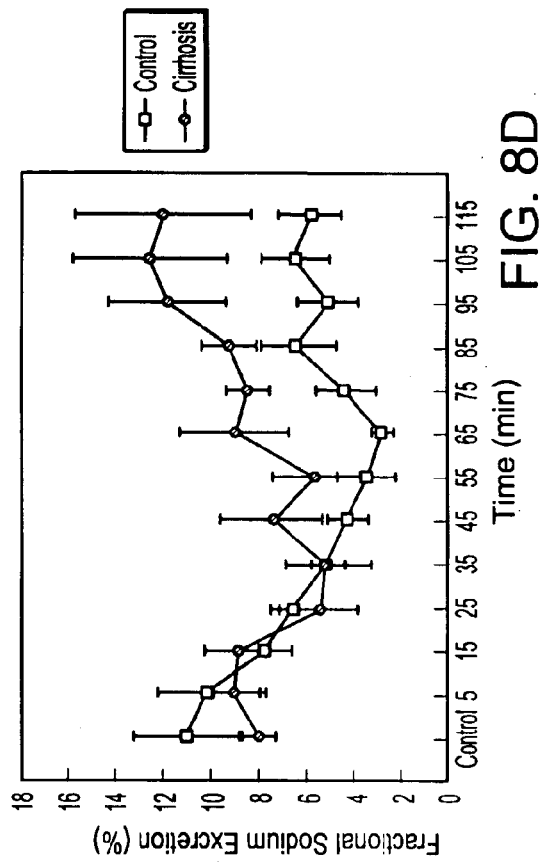
Figure 8A:
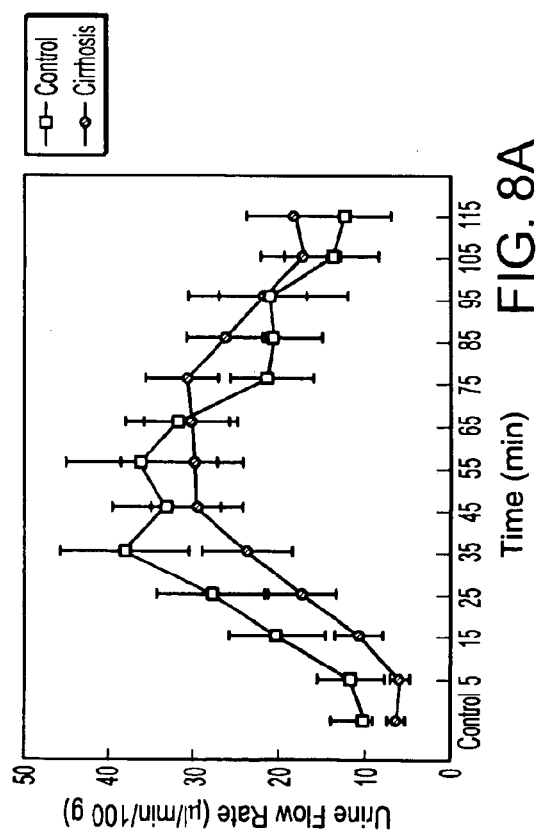
Figure 8C:
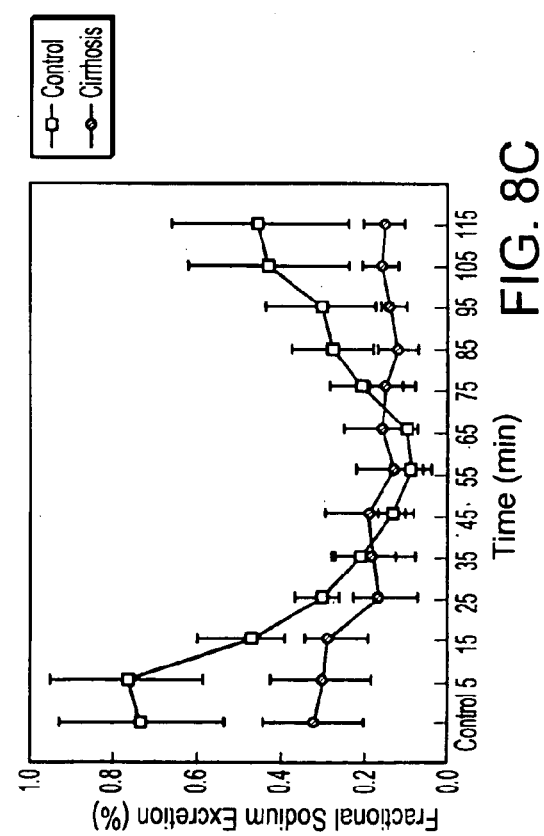

FIG. 6 illustrates the similar magnitude of changes in V and $U_{Na}V$ elicited by i.v. infusion of 0.1 nmol/kg/min Compound 1 and 1.1 nmol/kg/min of nociceptin. Together the data presented in FIGS. 5 and 6 suggest that Compound 1 compared to authentic nociceptin is approximately 10-fold more potent in producing similar magnitude diuretic and antinatriuretic responses. The diuretic effect of Compound 1 infusion tended to persist for a greater duration than that of i.v. nociceptin infusion.

Furthermore, the effects of i.v. bolus administration of nociceptin (30 and 100 nmol/kg, Phoenix Pharmaceuticals) and nociceptin-NH$_2$ (30 nmol/kg) on heart rate, arterial pressure and RSNA were studied in groups of 6 conscious Sprague-Dawley rats. The bolus injection produced rapid bradycardia, a hypotensive response and initial RSNA suppression (data not shown). A similar i.v. bolus injection of Compound 1 (30 nmol/kg) did not produce any changes in heart rate, blood pressure or RSNA. In addition, rats tested at this dose do not show any signs of stimulation of appetite or behavioral changes. The i.v. bolus injection of Compound 1 (30 nmol/kg) in this same rat produced a marked diuretic (V) and antinatriuretic (UNaV) response (data not shown). A summary of in vivo responses to Compound 1 obtained in the experiments described above are shown in Table 3 below:

TABLE 3

In vivo responses from series of experiments where

| I.v. dose of Compound 1 | HR | MAP | V | $U_{Na}V$ | $C_{H2O}$ | Food intake | Behavioral changes |
|---|---|---|---|---|---|---|---|
| I.v. infusion 0.1 nmol/kg/min | 0 | (↓) | ↑ | 0 | ↑ | 0 | 0 |
| I.v. infusion 1.0. nmol/kg/min | 0 | (↓) | ↑↑ | ↓ | ↑↑ | 0 | 0 |
| I.v. bolus injection 30 nmol/kg | 0 | 0 | ↑ | ↓ | ↑ | 0 | 0 |

0 indicates a lack of response, (↓) indicates a very weak decrease, ↓ indicates a weak decrease, ↑ indicates a weak increase, and ↑↑ indicates a strong increase.

From these studies it appears that Compound 1 evokes a significant diuretic response at i.v. infusion doses well below that required to evoke feeding or behavioral changes (e.g., sedation, increased exploratory behavior, catalepsy, convulsion etc.). Furthermore, after 120 min of i.v. infusion of Compound 1 (1 nmol/kg/min) in the study presented in FIG. 3, the HR and MAP responses to an i.v. bolus injection of nociceptin were examined. In these studies, the typical bradycardia and hypotension (rapid in onset and large in magnitude) was completely blocked in all rats tested (n=6).

In an additional series of dose-response studies, the cardiovascular and renal responses to Compound 1 were investigated after either i.v. bolus injection (10 (n=6), 30 (n=4), 100 (n=6) or 300 (n=4) nmol/kg i.v.) or during continuous i.v. infusion (0.1 (n=6), 1 (n=6) or 10 nmol/kg/min (n=6)). After stabilization of urine flow rate and urinary sodium excretion, urine was collected during a 20-min control period. After this, the i.v. bolus injection was given or the i.v. infusate was switched to a solution of isotonic saline containing Compound 1 (i.v. infusion experiments). From the time of drug administration, experimental urine samples (10-min consecutive periods) were taken for 80 min.

Feeding Response Observations

One hour prior to the start of each experiment a food pellet (standard rodent chow) was placed within access to the rat though a hole in the rat holder. The number and time of feeding responses (i.e., times in which the rat began to eat the food pellet) was recorded before, and after drug administration. If a positive feeding response was observed, the pellet was removed from the restrainer to prevent feeding-induced alterations in heart rate and/or mean arterial pressure. At 10-min intervals, the food pellet was presented to the rat to determine the duration of the feeding response.

In this series of studies in conscious, chronically catheterized rats, we have demonstrated that i.v. bolus injection of Compound 1 produces a selective water diuresis. Data are presented in Table 4 below:

TABLE 4

Responses after i.v. bolus administration of Compound 1

| Parameters studied | I.v. bolus dose (nmol/kg) | | | |
|---|---|---|---|---|
| | 10 (n = 6) | 30 (n = 4) | 100 (n = 6) | 300 (n = 4) |
| Δ Urine Flow (%) | +83 ± 42 | +207 ± 11 | +249 ± 60 | +127 ± 47 |
| Δ Na excretion (%) | −44 ± 3 | −51 ± 7 | −70 ± 2 | −85 ± 6 |
| Δ K excretion (%) | −35 ± 4 | −20 ± 7 | −52 ± 5 | −79 ± 6 |

TABLE 4-continued

Responses after i.v. bolus administration of Compound 1

| Parameters studied | I.v. bolus dose (nmol/kg) | | | |
|---|---|---|---|---|
| | 10 (n = 6) | 30 (n = 4) | 100 (n = 6) | 300 (n = 4) |
| Δ Blood Pressure (%) | −4 ± 1 | −8 ± 2 | −12 ± 2 | −15 ± 3 |
| Food intake | − | (+)* | (+)** | (+)*** |

*Indicates that of 4 rats tested at 30 nmol/kg, i.v. bolus, 1 rat demonstrated a feeding response at various time points throughout the 80-min experimental period.
**Indicates that of 6 rats tested at 100 nmol/kg, i.v. bolus, 3 rats evoked a feeding response within 30-min of i.v. bolus ZP120C administration. A feeding response was not observed over the testing period (80-min) in the remaining 3 rats.
***Indicates that of 4 rats tested at 300 nmol/kg, i.v. bolus, 2 rats demonstrated a feeding response at various time points throughout the 80-min experimental period.

When administered as a continuous i.v. infusion, a selective water diuretic response (diuresis associated with antinatriuresis) was observed at 1 and 10 nmol/kg/min (Table 5).

TABLE 5

Responses during i.v. infusion of Compound 1

| Parameters studied | I.v. infusion dose (nmol/kg/min) | | |
|---|---|---|---|
| | 0.1 (n = 6) | 1.0 (n = 6) | 10 (n = 6) |
| Δ Urine Flow (%) | +99 ± 21 | 210 ± 51 | 160 ± 68 |
| Δ Na excretion (%) | −5 ± 3 | −64 ± 7 | −79 ± 6 |
| Δ K excretion (%) | −16 ± 6 | −51 ± 9 | −68 ± 15 |
| Δ Blood Pressure (%) | −5 ± 4 | −10 ± 2 | −15 ± 3 |
| Food intake | − | − | (+)* |

*Indicates that of 6 rats tested at 10 nmol/kg/min, 4 rats did not evoke a feeding response and 2 rats ate in the last 10-min period of the 80-min infusion study.

Collectively, these dose-response studies demonstrate that Compound 1 produces a significant water diuretic response at i.v. infusion and i.v. bolus injection doses that are well below those required to elicit marked changes in cardiovascular function. This is in contrast to the diuresis produced by endogenous nociceptin, which is proceeded by a marked bradycardic and hypotensive response (i.v. bolus and i.c.v. injection), and a concurrent inhibition of renal sympathetic nerve activity (i.c.v. injection), [8–10]. These observations suggest that unlike the endogenous ORL1 ligand, nociceptin, Compound 1 has clinical utility as an aquaretic in patients at therapeutic doses substantially below those required to evoke adverse systemic cardiovascular events. We speculate that less penetration of Compound 1 into the CNS may explain the more selective renal effect of the novel compound compared to endogenous nociceptin.

Rats with liver cirrhosis induced by common bile duct ligation develop avid sodium and water retention and ascites within 2–4 weeks. The disturbed sodium and water balance in cirrhotic rats is in agreement with the pivotal clinical findings of edema and ascites in patients with liver cirrhosis. To examine the efficacy of Compound 1 in an experimental model of an edema-forming state, the diuretic response to an acute i.v. bolus injection of Compound 1 (65 nmol/kg) was evaluated in rats with liver cirrhosis induced by common bile duct ligation 4 weeks earlier. Prior to the experiments, rats were instrumented with chronic catheters in the urinary bladder, and in the femoral vein and artery. Renal responses to Compound 1 were compared with responses in sham-operated control rats. Compound 1 produced a marked increase in free water clearance (water diuresis), associated with a decrease in urinary excretion of sodium and potassium in the absence of changes in the glomerular filtration rate in all animals. The renal responses were similar in cirrhotic and control rats. Relative changes in urine flow rate, sodium and potassium excretion after i.v. administration of 65 nmol/kg in sham-operated control animals are summarized in FIG. 7.

As illustrated in FIG. 8, cirrhotic rats had a significantly lower fractional sodium excretion prior to drug administration relative to control animals. This indicates that the cirrhotic rats had severe sodium retention, which is in accordance with the marked sodium retention that characterizes human liver cirrhosis. Compound 1 produced a marked increase in urine flow rate, and free water clearance (water diuresis), associated with a decrease in fractional excretion of sodium and potassium in the absence of changes in the glomerular filtration rate in all animals. The renal responses were similar in cirrhotic and control rats. Changes in urine flow rate, free water clearance, fractional sodium excretion and fractional potassium excretion after i.v. administration of 65 nmol/kg in sham-operated control and cirrhotic animals are summarized in FIG. 8. These results in an animal model of a pathological state characterized by avid sodium retention indicate that compounds of the present invention, such as Compound 1, are useful in the treatment of edema, hypokalemia, and hyponatremia in edema-forming states such as liver cirrhosis, congestive heart failure, nephrotic syndrome and renal failure.

To evaluate whether acute tachyphylaxis develops during i.v. treatment with Compound 1, an additional series of experiments were performed. Chronically instrumented rats were infused with vehicle (150 mM glucose) or Compound 1 (1 nmol/kg/min) for twelve hours while water balance was maintained using a computer-driven, servo-controlled i.v. volume replacement system [2]. Acute tachyphylaxis has been observed during repeated i.v. dosing of the vasopressin antagonist SKF 101926 in conscious dogs [12] and tolerance during chronic treatment has been reported for the selective $V_2$-receptor antagonist OPC-31260 [13].

Figure 9:
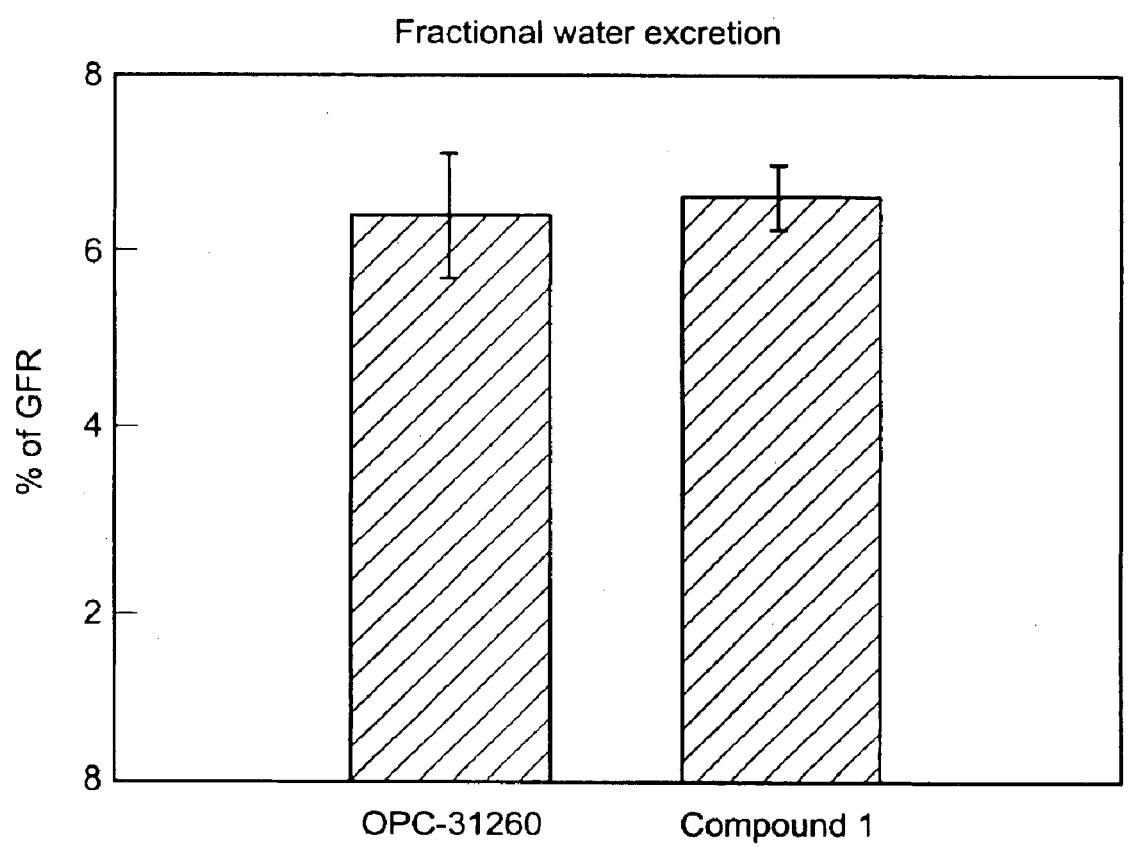
FIG. 9 is an illustration of the fractional excretion of water (V/GFR) during steady-state i.v. infusion with a maximal aquaretic dose of the selective vasopressin type-2 receptor antagonist OPC-31260 (0.8 mg/kg/h; n=8 (data from [2]) or Compound 1 (12 nmol/kg/min). In order to prevent activation of compensatory volume homeostatic mechanisms, experiments were performed during conditions whereby volume depletion was prevented by computer-driven, servo-controlled intravenous volume replacement with 150 mM glucose.

Compound 1 elicited a sustained aquaretic response lasting the entire 12-hour infusion period suggesting that acute tachyphylaxis does not develop during treatment with this compound. I.v. infusion of 1 nmol/kg/min of Compound 1 elicited an aquaretic response of similar magnitude to the response seen with maximal doses of the selective vasopressin type-2 receptor antagonist OPC-31260 (FIG. 9) when tested in the same model [2]. In this experiment, 1 nmol/kg/min of Compound 1 inhibited tubular water reabsorption without concomitant changes in arterial blood pressure, heart rate, renal blood flow, glomerular filtration rate or proximal tubular reabsorption. These experiments demonstrated that Compound 1 has a maximal aquaretic efficacy similar to what can be obtained with vasopressin type-2 antagonists. However, no acute tachyphylaxis develops within the first 12 hours of treatment with Compound 1 and this finding represents a further therapeutic advantage of Compound 1 relative to vasopressin type-2 receptor antagonists. Moreover, vasopressin type-2 receptor antagonists do not affect renal handling of electrolytes, while compounds of the present invention decrease urinary excretion of sodium and potassium.

To examine the effect of compounds of the present invention in an in vivo model of heart failure a chronic model of low-output heart failure will be used. Briefly, the rats will be anaesthetized in an inhalation chamber with 4% halothane in 1:1 $N_2O/O_2$ gas mixture. After insertion of an endotracheal tube the animal is artificially ventilated with 1% halothane in a 1:1 $N_2O/O_2$ gas mixture. Tidal volume and respiratory rate are adjusted to maintain arterial pH between 7.35 and 7.45. During surgery the animal is placed on a heated table that maintained rectal temperature at 37–38° C. Left coronary artery ligation, used to produce congestive heart failure is performed via a parasternal thoracotomy and a 6-0 silk suture is placed between the pulmonary trunk and the left auricle. Sham-operation is performed without ligating the left coronary artery. To minimize postsurgical pain, rats are treated postoperatively with buprenorphine 0.2 mg/kg s.c.b.i.d. for 2 days. Two weeks after heart surgery permanent Tygon catheters are inserted into the femoral artery and vein, and a bladder catheter is inserted into the urinary baldder. To prevent coagulation in vascular catheters, these lines are filled with 50% dextrose with 1,000 units heparin/ml and 10,000 units streptokinase/ml. Inventors of the present invention have previously described the use of this model [14]. Physiological examinations are performed 3 weeks after heart surgery since the functional deterioration after left coronary artery ligation is generally maximal at this time. Renal function studies are performed as described above. To evaluate the degree of heart failure, the rat is anaesthetized with halothane in 1:1 $N_2O/O_2$, intubated and artificially ventilated, and a Tygon catheter is inserted into the left ventricle via the right carotid artery for measurement of left ventricular end-diastolic pressure (LVEDP). Accurate measurement of LVEDP is performed by adjusting the concentration of halothane to maintain after-load during anaesthesia at the same level as mean arterial pressure recorded in the conscious state. This animal model shares clinical features of low cardiac output, sodium and water retention, and edema formation with the most common form of human heart failure [15].

To examine the effect of compounds of the present invention in an in vivo model of nephritic syndrome a chronic model of adriamycin-induced nephritic syndrome will be used. Nephrotic syndrome is induced with a single intravenous injection of adriamycin (=doxorubicin, Sigma Chemical, St. Louis, Mo.); 7–8 mg/kg at a concentration of 10 mg/ml dissolved in normal saline. In this model, proteinuria begins 4 to 5 days after a single intravenous injection of 7.5 mg/kg. The full expression of the syndrome with glomerular changes, proteinuria, sodium and water retention, and edema-formation develops 13 to 15 days later [15;16].

To examine the effect of compounds of the present invention in an in vivo model of liver cirrhosis a chronic model of biliary cirrhosis induced by common bile duct ligation will be used[17]. After 28 days of obstruction, the rats develop a progressive cirrhosis that is associated with sodium and water retention, and ascites [15].

To examine the effect of compounds of the present invention in an in vivo model of multiple organ failure including acute renal failure, a model of organ failure elicited by hemorrhage during anesthesia and surgery will be used. In this model, rats are infused with isotonic saline or compounds of the present invention for 15 min prior to anesthesia. Then the animals are anestetized with isoflurane (3% in $O_2/N_2O$ mixture) and subjected to periods of surgery (chronic bladder catheterization+femoral vein and artery; 30 min); hemorrhage (20 cc/kg b.w.; 45 min), and recovery (blood replacement; 120 min). Consecutive 10 min urine samples are collected throughout, and rats are allowed to recover for 7 days. Following the hemorrhagic event, urine collections and blood samples are collected (e.g., days 2, 4, and 6) to evaluate the recovery as determined by urine production, and serum concentrations of creatinine and urea. Finally on day 7, rats are sacrified for histological examination of all organs. Using this model, Kapusta et al. previously demonstrated that the kappa opioid agonist U-50, 488H prevents multiple organ failure (kidney, lungs, intestines) and increases survival after a hemorrhagic event elicited during surgical anaesthesia [18].

In summary, in vivo studies have demonstrated that Compound 1 is a potent sodium and potassium-sparing aquaretic. In addition to its peripheral effects, nociceptin elicits a centrally mediated decrease in sympathetic nerve activity, arterial blood pressure and heart rate [10;19;20]. Moreover, nociceptin decreases spinal sympathetic outflow by depressing the activity of spinal preganglionic neurons both in vitro and in vivo [21]. The rapid onset and similar time relationship of decreased sympathetic nerve activity, blood pressure and heart rate in rats with sinoaortic baroreceptor denervation suggest that the cardiovascular effects of nociceptin is largely mediated by inhibition of sympathetic nerve activity to the cardiovascular system [10]. Thus, the inhibitory action of Compound 1 on nociceptin-induced hypotension and bradycardia suggests that Compound 1 is able to antagonize the effects of nociceptin on neurogenic control of heart rate and blood pressure. The finding that Compound 1 acts as a nociceptin antagonist in vivo is supported by the fact that Compound 1 antagonizes the smooth muscle relaxing effect of nociceptin in the mouse vas deferens model. Thus, in contrast to endogenous nociceptin, Compound 1 increases urine flow rate and decreases urinary excretion of sodium and potassium in doses that do not produced marked bradycardia and hypotension.

In Vitro Studies of the Binding of Compound 1 to ORL1

In a series of binding assays we have demonstrated that Compound 1 binds to the human nociceptin receptor (i.e, ORL1) with high affinity and high specificity.

Using HEK293 cells that were transfected with the human ORL1 receptor, we have demonstrated that Compound 1 displaces the specific binding of [3H]-labeled nociceptin with a $K_I$=0.26 nM.

In addition, Compound 1 has been tested in 5 opioid (non-selective opiate, δ, κ, μ, &ORL1), 3 vasopressin ($V_{1a}$, $V_{1b}$ and $V_2$) receptor binding assays at 0.1, 10, and 1000 nM as well as in 40 different receptor, uptake, and ion channel binding sites ($A_1$, $A_2$, $α_1$, $α_2$, $β_1$, NE uptake, $AT_1$, BZD, $B_2$ (h), $CCK_A$ (∼$CCK_1$), D1, D2, $ET_A$(h), GABA, NMDA, $H_1$, M, $NK_1$(h), Y, N, opiate, PCP, 5-HT, $5-HT_{1B}$, $5-HT_{2A}$, 5-HT uptake, σ, $V_1$) at 10 μM. These experiments demonstrated that Compound 1 is a selective ORL1 receptor ligand with none or only weak binding to other receptors than the ORL1 receptor. Moreover, in transfected HEK293 cells that express the human ORL1 receptor, Compound 1 inhibits forskoline-induced formation of cAMP with an $EC_{50}$=0.54 nM and a relative maximum relative to nociceptin of 92%. These results suggest that Compound 1 is a selective ORL1 receptor agonist.

Data showing the binding of compounds of the invention to the human ORL1 receptor expressed in CHO cells calculated as $IC_{50}$ (nM) values (all based on one experiment) are shown in Table 6 below. The ORL1 receptor is negatively coupled to cAMP and thus the effect of ORL1 agonists are detected as an inhibition of forskolin-incuced cAMP formation. Six compounds of the invention have been tested for efficacy on hORL1 receptor expressed in CHO cells. The $EC_{50}$ (nM) values are all based on one experiment (data shown in Table 6).

TABLE 6

Binding of ZS-compounds (peptides) on hORL1 receptor

| Compound number | Binding IC$_{50}$ (nM) | Efficacy EC$_{50}$ (nM) |
|---|---|---|
| CE1 | 0.31 | 0.41 |
| 1 | 0.32 | 0.58 |
| 3 | 235 | 83 |
| 4 | ND | 91 |
| 6 | 115 | 135 |
| 7 | >100 | ND |
| 8 | 78 | 59 |
| 9 | 3.7 | 0.035 |
| 10 | 0.51 | ND |
| 11 | 0.27 | ND |
| 12 | 0.15 | ND |
| 13 | ND | ND |

ND = not determined

Most of the published work concerning the human ORL1 receptor has been focused on the CNS effects of the receptor. However, the work described herein is focused on the effect mediated by Compound 1 in the kidney. In order to determine whether the ORL1 receptor is present in the human kidney, we have constructed PCR primers homologous to the ORL1 receptor expressed in the human brain. Total RNA isolated from human kidney RNA was subjected to first strand synthesis to obtain material for PCR analysis. This analysis showed a 449 bp fragment of the ORL1 receptor indicating that the receptor is expressed in the human kidney, and therefore, ORL1 ligands of the present are expected to have renal actions in humans.

In Vitro Stability

Degradation of peptides is almost exclusively seen in the presence of enzymes, e.g. in the bloodstream. An important feature of a putative drug is whether it is quickly degraded in vivo or whether it is able to conduct its effects over a longer period of time. To be able to examine the stability of the peptide conjugates of the present invention degradation was tested in heparin stabilised mouse plasma (obtained from Harlan Seralab, UK).

Methods

The stability studies were run in triplicate. 100 µL of a 1 mg/mL solution of the test compound (peptide conjugate) was added to an Eppendorf tube, containing 900 µL plasma, incubated at 37 C. Immediately after addition, a sample of 100 µL was removed and added to an Eppendorf tube, containing 10 µL of extraction solution (50% TFA (trifluoroacetic acid) in MeCN, v/v). This sample constitutes t=0. Subsequently, samples were removed at t=15, 30, 60, 120, 180, 240, 300, and 360 min and treated in the same manner as for t=0. The samples are centrifuged at 20,000×g, and the supernatant was transferred to vials and analysed by high-performance liquid chromatography (HPLC).

Figure 10:
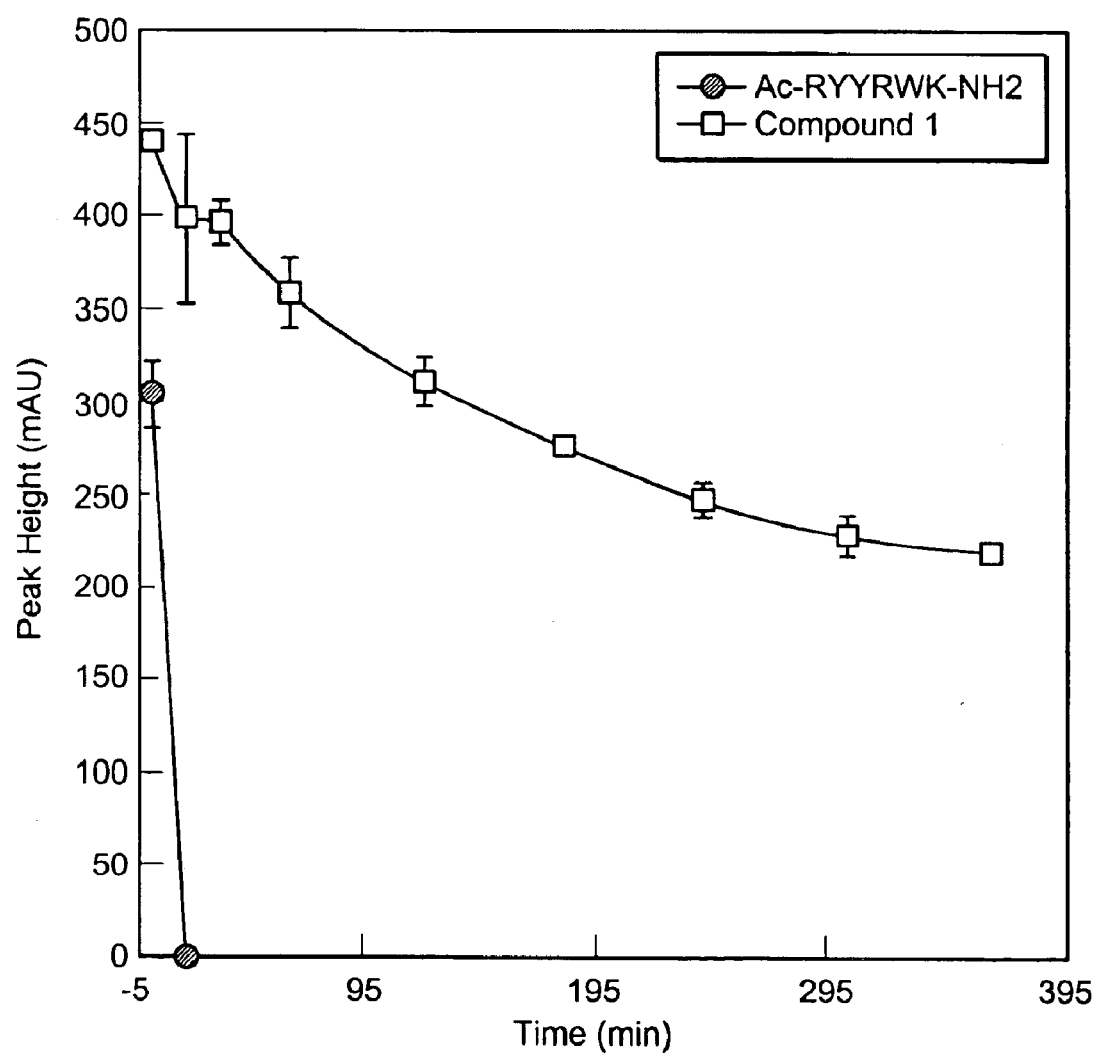
FIG. 10 is a graph showing the rate of degradation in heparinised mouse plasma of Compound 1 and Ac-RYYRWK-NH$_2$. (SEQ ID NO:1)

The analysis was performed on a HP1100 HPLC with a quaternary pump. The column used was a Vydac 201SP5215, and the apparatus comprises an autosampler, a column oven, a variable UV detector and a fluorescence detector. The process was controlled by ChemStation software. The gradient elution consisted of two solvents A and B, which contained 0.02% n-Heptafluorobutyric acid (HFBA) in MilliQ water (MQW) and 0.02% HFBA in 90% MeCN in MQW, respectively. The separation was performed at 30 C using a linear gradient from 5–100% B in 15 minutes at a flow of 0.250 mL/min. The chromatograms used in this study were obtained by UV detection at a wavelength of 254 nm. The peaks identified as the test peptides by comparison to known standards were integrated to yield peak area as a measure of concentration for each time point. These values were transferred to Microsoft Excel, where half-lives (t½) and rate constant (k$_{obs}$) for Ac-RYYRWK-NH$_2$ (SEQ ID NO:1) and Compound 1 were determined by fitting to the equation. As illustrated in FIG. 10 the rate of degradation of the unconjugated substance Ac-RYYRWK-NH$_2$ (SEQ ID NO:1) was significantly faster than for Compound 1 (Ac-RYYRWK-NH$_2$: t½=2–5 min (estimated) and Compound 1: t½=358+/−36 min).

These data demonstrate that the conjugated peptide Compound 1 is significantly more stable in heparinized mouse plasma than the unconjugated hexapeptide, Ac-RYYRWK-NH$_2$ (SEQ ID NO:1). Thus, the invention also relates to a method of enhancing the stability of a hexapeptide, preferably a hexapeptide of formula II herein, and more preferably the hexapeptide RYYRWK (SEQ ID NO:1), by linking a peptide sequence Z' as defined herein, preferably Z' is a K$_6$ sequence, via a peptide bond to the C-terminal of said hexapeptide.

Stability in Heparinised Human Plasma

In addition, the degradation of Compound 1 of the invention has been studied in heparinised human plasma. Table 7 below shows the half life of degradation (T½) of Compound 1 of the invention compared to Ac-RYYRWK-NH2 (SEQ ID NO:1 and nociceptin-NH2. It appears from the table that Compound 1 of the invention having a half life of more than 16 hours is considerably more stable in plasma than Ac-RYYRWK-NH2 (SEQ ID NO:1) which has a half life of less than 1 hour, and nociceptin-NH$_2$ which has a half life of about 1.5 hours.

TABLE 7

Results of in vitro stability test in plasma and serum, T$_{1/2}$ in minutes (mean ± deviation).

| COMPOUNDS | T$_{1/2}$ in min (degradation in human heparinised plasma) |
|---|---|
| Compound 1 | 973.8 min ± 21.9% |
| Ac-RYYRWK-NH$_2$ (SEQ ID NO:1) | 50.7 min ± 20.9% |
| Nociceptin-NH$_2$ | 97.5 min ± 6.4% |

\* no reaction over 5 hrs

Method of Analysis of In Vitro Plasma Stability

The stability of peptides is analysed in human plasma. The peptides are incubated at 37° C. in plasma and samples taken at approx. 8 regular intervals between t=0 and t=390 min for Compound 1 and nociceptin-NH$_2$, and at 9 intervals between t=0 and t=32 min for Compound CE1 are analysed by HPLC.

Appropriate conditions (column, solvent, gradient, and temp.) for the HPLC analyses are estimated to ensure that the drug peak and the plasma peaks do not have the same retention time. This is done by subsequent injections of the drug, plasma, and a co-injection with the drug and the plasma, followed by optimisation of the LC method parameters until a satisfactory separation is obtained. Three parallel experiments are performed for each plasma type. 100 µl of peptide is mixed with 900 µl plasma at t=0 and incubated at 37° C. (drug-plasma mixture conc. 0.1 mg/ml). Samples of 100 µl of the drug-plasma mixture are removed at appropriate intervals and the degradation stopped by precipitation of the sample with 10 µl MeCN:TFA 50:50 v/v. A control plasma sample without the drug treated in the same manner is also taken. The plasma samples are centrifuged for 15 min. at 12,000 rpm (Eppendorf centrifuge) at ambient temperature. The resulting supernatant solution is trans ferred to 300 µl HP autosamler vials and analyzed by HPLC. HPLC analysis are performed as follows:

Ac-RYYRWK-NH$_2$ (SEQ ID NO:1) and Compound 1
Column: Vydac 201SP5215, 991203, 033,
S/N N 905550-1-3, 150×2.1 mm, flow: 0.200 mL/min. Temp.: 40° C.
Solvent A: 0.02% HFBA in MQW. Solvent B: 0.02% HFBA in MQW:MeCN 10:90
Run time=25 min. Inj.vol.:20 µL. Detection: FLD1 A, Ex.=280 nm, Em.=335 nm
Gradient (time in min; %B): 0;5 5;50 15;100 15.5;5 25;5

Nociceptin-NH$_2$
Column: Vydac 218MSP52, 000517, 095,
S/N N 970520-9-7, 250×2.1 mm, flow: 0.200 mL/min. Temp.: 40° C.
Solvent A: 0.1% TFA in MQW. Solvent B: 0.1% TFA in MQW:MeCN 10:90
Run time=25 min. Inj.vol.:20 µL. Detection: MWD Signal=215.16 nm, ref.=360, 100 nm
Gradient (time in min; %B): 0;1 5;1 15;40 16;100 17;1 25;1

The samples are analysed in the following order: blank, the peptide at 0.1 mg/mL, the plasma without the peptide, the three parallel samples for t=0, the three parallel samples for t=5 min. the three parallel samples for t=60 min. etc. And finally the three parallel samples for t=0 are repeated to make sure that there have been no degradation or other failure during the analyses. The sample concentrations (peak height in mAU) are plotted vs. time and fitted to a function describing a mono exponential decay (Excel). The half-lives of the peptides in plasma are presented in Table 7 as mean (n=3) ± standard deviation.

Compositions

The invention also concerns a composition comprising a pharmacologically active peptide conjugate as defined herein in combination with a pharmaceutically acceptable carrier and/or diluent. Such compositions may be in a form adapted to oral, subcutaneous, parenteral (intravenous, intraperitoneal), intramuscular, rectal, epidural, intratracheal, intranasal, dermal, vaginal, buccal, ocularly, or pulmonary administration, preferably in a form adapted for administration by a peripheral route, or is suitable for oral administration or suitable for parenteral administration. Other preferred routes of administration are subcutaneous, intraperitoneal and intravenous, and such compositions may be prepared in a manner well-known to the person skilled in the art, e.g., as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker. The compositions may appear in conventional forms, for example, solutions and suspensions for injection, capsules and tablets, preferably in the form of enteric formulations, e.g. as disclosed in U.S. Pat. No. 5,350,741, for oral administration.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax.

When a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g.

A Typical Tablet Which May Be Prepared By Conventional Tabletting Techniques May Contain Core: active compound (as free compound or salt thereof) 100 mg; colloidal silicon dioxide (Aerosil) 1.5 mg; cellulose, microcryst. (Avicel) 70 mg; modified cellulose gum (Ac-Di-Sol) 7.5 mg; magnesium stearate. Coating: HPMC approx. 9 mg; Mywacett 9-40T (acylated monoglyceride used as plasticizer for film coating) approx. 0.9 mg.

When a liquid carrier is used, the preparation may be in the form of a syrup, emulsion, soft gelatin capsule or sterile injectable liquid such as an aqueous or non-aqueous liquid suspension or solution.

The composition may also be in a form suited for local or systemic injection or infusion and may, as such, be formulated with sterile water or an isotonic saline or glucose solution. It is preferred that the compositions of the invention are in a form adapted for peripheral administration only, with the exeption of centrally administrable forms.

The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

Formulation of Peptide Conjugate For Intravenous Injection

Multi-dose formulations may be prepared as a solution of a compound of the invention in sterile, isotonic saline, stored in capped vials, and if necessary a preservative is added (e.g. benzoates). Fixed dose formulations may be prepared as a solution of the compound in sterile, isotonic saline, stored in glass ampoules, and if necessary filled with an inert gas. Each dose of the compound is stored dry in ampoules or capped vials, if necessary filled with inert gas. The multi-dose formulation demands the highest degree of stability of the compound. When the stability of the compound is low fixed dose formulations can be used.

For nasal administration, the preparation may contain a compound of the present invention dissolved or suspended in a liquid carrier, in particular, an aqueous carrier, for aerosol application. The carrier may contain additives such as solubilizing agents, e.g., propylene glycol, surfactants such as bile acid salts or polyoxyethylene higher alcohol ethers, absorption enhancers such as lecithin (phosphatidylcholine) or cyclodextrin, or preservatives such as parabines.

In a preferred embodiment of the invention the compound of formula I, II or III is administered as a dose in the range from about 0.001 to about 10 g per patient per day, preferably from about 1 to about 1000 mg per patient per day, more preferably from about 10 to about 100 mg per patient per day, about 50 mg per patient per day. A pharmaceutical composition adapted for oral administration typically contains in a unit dosage an amount of a compound of formula I or II ranging from about 1 to about 100 mg. A pharmaceutical composition adapted for parenteral administration typically contains in a unit dosage an amount of a compound of formula I or II ranging from about 0.1 to about 10 mg.

The invention also concerns a pharmacologically active compound which is a peptide conjugate or a derivative or salt thereof as disclosed herein for use in therapy, and the use thereof as defined herein for the manufacture of a pharmaceutical composition for use in therapy, e.g., in the treatment of ORL1 related peripheral diseases and ailments. Preferably, a pharmaceutical composition is suitale for oral administration. Therapeutic uses of the novel peptide conjugates herein are to increase the renal excretion of water and to decrease urinary sodium and potassium excretion (i.e., a selective water diuresis) using relatively low doses of the active compound, i.e. preferably less than 50 mg per patient per day, and to decrease blood pressure in absence of reflex tachycardia and increase appetite using higher doses of the active compound.

In specific embodiments, a peptide conjugate according to the present invention may be used to avoid CNS side effects due to poor penetration of the peptide conjugates into the central nervous system, in the treatment of specific diseases or ailments amenable to treatment with compounds having nociceptin-like activity.

In specific embodiments, a peptide conjugate according to the present invention may be used as an agonist or partial agonist or as an inhibitor depending on clinical utility acting on a nociceptin receptor, such as ORL1, especially where said receptor is found in peripheral tissue. Thus, the peptide conjugate of formula I or III is useful for the preparation of a medicament to be used in the treatment of disease states associated with elevated tone of nociceptin.

In specific embodiments, a peptide conjugate according to the present invention may be used for the preparation of a medicament for the treatment and/or prevention of hyponatremia and/or hypokalemia as well as in a method of treating and/or preventing hyponatremia and/or hypokalemia.

Furthermore, a peptide conjugate according to the present invention may be used for the preparation of a medicament for the treatment and/or prevention of sodium and water retaining conditions and acute renal failure as well as in a method of treating and/or preventing multiple organ failure and sodium and water retaining conditions and acute renal failure. Furthermore, a peptide conjugate according to the present invention may be used for the preparation of a medicament for the treatment and/or prevention of organ failure conditions associated with extracellular fluid volume expansion which include:

1. Congestive heart failure in which the heart failure may be described as systolic or diastolic, high-output or low-output, acute or chronic, right-sided or left-sided, and forward or backward. An example of a predictive in vivo heart failure model for the study of therapeutic actions of peptides of the present invention is the conscious rat model of low-cardiac output induced by ligation of the left coronary artery [15] which is incorporated by reference.
2. Liver cirrhosis in which the cirrhosis may be related to alcoholic liver disease; postnecrotic cirrhosis (caused by infectious diseases, inherited metabolic disorders, drugs and toxins, inflammatory and other diseases); biliary cirrhosis (primary or secondary); cardiac cirrhosis due to prolonged, severe right-sided congestive heart failure; metabolic, hereditary, drug-related or other types of cirrhosis. An example of a predictive in vivo model of liver cirrhosis for the study of therapeutic actions of peptides of the present invention is the conscious rat model of liver cirrhosis induced by ligation of the common bile duct [15].
3. Nephrotic syndrome related to systemic and/or renal disease, drug- or toxin-induced. An example of a predictive in vivo model of nephritic syndrome for the study of therapeutic actions of peptides of the present invention is the conscious rat model of nephritic syndrome induced by i.v. administration of adriamycin [15].
4. Hypertension in which the hypertension may be primary (idiopathic) or secondary to drugs, toxins or diseases in endocrine glands, kidneys, or in the central nervous system. Examples of predictive in vivo models of hypertension for the study of therapeutic actions of peptides of the present invention is the spontaneously hypertensive rat or the Dahl salt-sensitive rat.
5. Multiple organ failure elicited during hemorrhagic shock including acute renal failure. An example of a predictive in vivo model of multiple organ failure (kidney, lungs, intestines) elicited during anaesthesia, surgery and hemorrhage is described by Kapusta et al. [18] which is incorporated by reference.
6. Acute renal failure in which the pathogenesis of the disease may be related to either prerenal or intrinsic renal causes:

Prerenal azotemia, such as the following conditions:
I. Hypovolemia
  A. Hemorrhage, burns, dehydration
  B. Gastrointestinal fluid loss: vomiting, surgical drainage, diarrhea
  C. Renal fluid loss: diuretics, osmotic diuresis (e.g., diabetes mellitus), hypoadrenalism
  D. Sequestration in extravascular space: pancreatitis, peritonitis, trauma, burns, severe hypoalbuminemia;
II. Low cardiac output
  A. Diseases of myocardium, valves, and pericardium, arrhythmias, tamponade
  B. Other: pulmonary hypertension, massive pulmonary embolus, positive pressure mechanical ventilation;
III. Altered renal systemic vascular resistance ratio
  A. Systemic vasodilatation: sepsis, antihypertensives, afterload reducers, anesthesia, anaphylaxis
  B. Renal vasoconstriction: hypercalcemia, norepinephrine, epinephrine, cyclosporine, amphotericin B
  C. Cirrhosis with ascites (hepatorenal syndrome);
IV. Renal hypoperfusion with impairment of renal autoregulatory responses
  Cyclooxygenase inhibitors, angiotensin-converting enzyme inhibitors;
V. Hyperviscosity syndrome (rare)
  Multiple myeloma, macroglobulinemia, polycythemia.

Acute renal failure further include:
Intrinsic renal azotemia, such as the following conditions:
I. Renovascular obstruction (bilateral or unilateral with one functioning kidney)
  A. Renal artery obstruction: atherosclerotic plaque, thrombosis, embolism, dissecting aneurysm, vasculitis
  B. Renal vein obstruction: thrombosis, compression;
II. Disease of glomeruli or renal microvasculature
  A. Glomerulonephritis and vasculitis
  B. Hemolytic uremic syndrome, thrombotic thrombocytopenic purpura, disseminated intravascular coagulation, toxemia of pregnancy, accelerated hypertension, radiation nephritis, systemic lupus erythematosus, scleroderma;

III. Acute tubular necrosis
  A. Ischemia: as for prerenal azotemia (hypovolemia, low cardiac output, renal vasoconstriction, systemic vasodilatation), obstetric complications (abruptio placentae, postpartum hemorrhage)
  B. Toxins
    1. Exogenous: radiocontrast, cyclosporine, antibiotics (e.g., aminoglycosides), chemotherapy (e.g., cisplatin), organic solvents (e.g., ethylene glycol), acetaminophen, illegal abortifacients
    2. Endogenous: rhabdomyolysis, hemolysis, uric acid, oxalate, plasma cell dyscrasia (e.g., myeloma);

IV. Interstitial nephritis
  A. Allergic: antibiotics (e.g., -lactams, sulfonamides, trimethoprim, rifampicin), nonsteroidal anti-inflammatory agents, diuretics, captopril
  B. Infection: bacterial (e.g., acute pyelonephritis, leptospirosis), viral (e.g., cytomegalovirus), fungal (e.g., candidiasis)
  C. Infiltration: lymphoma, leukemia, sarcoidosis
  D. Idiopathic;

V. Intratubular deposition and obstruction
  A. Myeloma proteins, uric acid, oxalate, acyclovir, methotrexate, sulphonamides;

VI. Renal allograft rejection

Examples of predictive in vivo models of prerenal azotemia for the study of therapeutic actions of peptides of the present invention are the norepinephrine and renal artery clamp rat ischemic acute renal failure models, that may be accelerated by hemorrhage [22] which is incorporated by reference.

An example of a predictive in vivo model of intrinsic renal azotemia for the study of therapeutic actions of peptides of the present invention is the gentamicin-induced acute renal failure model [23] which is incorporated by reference.

REFERENCES

[1.] C. T. Dooley, C. G. Spaeth, I. P. Berzetei-Gurske, K. Craymer, I. D. Adapa, S. R. Brandt, R. A. Houghten, L. Toll, *J Pharmacol.Exp. Ther.* 1997, 283 735–741.

[2.] T. E. Jonassen, S. Christensen, T. H. Kwon, S. Langhoff, N. Salling, S. Nielsen, *Am J Physiol Renal Physiol* 2000, 279 F1101–F1109.

[3.] E. Braunwald, in *Harrison's Principles of INternal MedicineEds.*: A. S. Fauci, E. Braunwald, K. J. Isselbacher, J. D. Wilson, J. B. Martin, D. L. Kasper, S. L. Hauser, D. L. Longo), McGraw-Hill, N.Y. 1998, p. pp. 1287–1298.

[4.] J. Hughes, H. W. Kosterlitz, F. M. Leslie, *Br.J Pharmacol.* 1975, 53 371–381.

[5.] Smith, C. B. NIDA Research Monograph. [76], 288–294. 1987.
Ref Type: Serial (Book,Monograph)

[6.] G. Calo, A. Rizzi, G. Bogoni, V. Neugebauer, S. Salvadori, R. Guerrini, C. Bianchi, D. Regoli, *Eur.J Pharmacol.* 1996, 311 R3–R5.

[7.] Kenakin, T. Pharmacological Analysis of Drug-Receptor Interaction. 2nd. 1993. USA, Raven Press.
Ref Type: Serial (Book,Monograph)

[8.] D. R. Kapusta, S. F. Sezen, J. K. Chang, H. Lippton, V. A. Kenigs, *Life Sci.* 1997, 60L15–L21.

[9.] D. R. Kapusta, *Peptides* 2000, 21 1081–1099.

[10.] D. R. Kapusta, V. A. Kenigs, *Am J Physiol* 1999, 277 R987–R995.

[11.] H. C. Champion, R. L. Pierce, P. J. Kadowitz, *Regul.Pept.* 1998, 78 69–74.

[12.] G. G. Liversidge, C. G. Wilson, W. L. Sternson, L. B. Kinter, *J Appl.Physiol* 1988, 64 377–383.

[13.] T. E. N. Jonassen, S. Christensen, J. S. Petersen, *J.Am.Soc.Nephrol.* 1997, 8 19A.

[14.] S. Nielsen, J. Terris, D. Andersen, C. Ecelbarger, J. Frokiaer, T. Jonassen, D. Marples, M. A. Knepper, J. S. Petersen, *Proc.Natl.Acad.Sci.U.S.A* 1997, 94 5450–5455.

[15.] G. F. DiBona, P. J. Herman, L. L. Sawin, *Am J Physiol* 1988, 254 R1017–R1024.

[16.] T. Bertani, A. Poggi, R. Pozzoni, F. Delaini, G. Sacchi, Y. Thoua, G. Mecca, G. Remuzzi, M. B. Donati, *Lab Invest* 1982, 46 16–23.

[17.] J. Kountouras, B. H. Billing, P. J. Scheuer, *Br.J Exp.Pathol.* 1984, 65 305–311.

[18.] D. R. Kapusta, V. A. Kenigs, L. A. Dayan, A. W. Dreisbach, S. Meleg-Smith, V. Batuman, K. J. Varner, *J.Am-.Soc.Nephrol.* 2000, 11 A3175.

[19.] T. Shirasaka, T. Kunitake, K. Kato, M. Takasaki, H. Kannan, *Am J Physiol* 1999, 277 R1025–R1032.

[20.] D. R. Kapusta, J. K. Chang, V. A. Kenigs, *J Pharmacol.Exp.Ther.* 1999, 289 173–180.

[21.] C. C. Lai, S. Y. Wu, C. T. Chen, N. J. Dun, *Am J Physiol Regul.Integr.Comp Physiol* 2000, 278 R592–R597.

[22.] J. D. Conger, M. F. Schultz, F. Miller, J. B. Robinette, *Kidney Int.* 1994, 46 318–323.

[23.] D. de Rougemont, A. Oeschger, L. Konrad, G. Thiel, J. Torhorst, M. Wenk, P. Wunderlich, F. P. Brunner, *Nephron* 1981, 29 176–184.

Preparation of Peptides

The peptides or peptide conjugates herein are preferably prepared using peptide synthetic methods but may also be prepared by means of recombinant DNA-technology using general methods and principles known to the person skilled in the art. Thus the present invention also relates to a nucleic acid sequence encoding a polypeptide sequence comprising the peptide sequence of formula I or III; a vector carrying said nucleic acid sequence, and a host cell comprising said nucleic acid sequence and capable of expressing said polypeptide sequence.

A nucleic acid sequence encoding the present peptide conjugate may be prepared synthetically by established standard methods, e.g., the phosphoamidite method described by S. L. Beaucage and M. H. Caruthers, Tetrahedron Letters 22, 1981, pp. 1859–1869, or the method described by Matthes et al., EMBO Journal 3, 1984, pp. 801–805. According to the phosphoamidite method, oligonucleotides are synthesized, e.g., in an automatic DNA synthesizer, purified, annealed, ligated and cloned in suitable vectors. The techniques used to isolate or clone a nucleic acid sequence encoding the peptide X are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, A Guide to Methods and Application, Academic Press, New York. Other nucleic acid amplification procedures such as ligase chain reaction (LCR), ligated activated transcription (LAT) and nucleic acid sequence-based amplification (NASBA) may be used. It can then be ligated to a nucleic acid sequence encoding Z.

The nucleic acid sequence encoding the conjugate is then inserted into a recombinant expression vector which may be any vector which may conveniently be subjected to recombinant DNA procedures. The choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. In the vector, the nucleic acid sequence encoding the conjugate of the present invention should be operably connected to a suitable promoter sequence. The promoter may be any nucleic acid sequence which shows transcriptional activity in the host cell of choice and may be derived from genes encoding proteins either homologous or heterologous to the host cell. Examples of suitable promoters for directing the transcription of the nucleic acid sequence encoding the conjugate, especially in a bacterial host cell, are the promoters obtained from the *E. coli lac* operon, the *Streptomyces coelicolor agarase* gene (dagA), and the *prokaryotic beta-lactamase* gene (Villa-Kamaroff et al., 1978, Proceedings of the National Academy of Sciences USA 75:3727–3731), as well as the tac promoter (DeBoer et al., 1983, Proceedings of the National Academy of Sciences USA 80:21 25). Further promoters are described in "Useful proteins from recombinant bacteria" in Scientific American, 1980, 242:74–94; and in Sambrook et al., 1989, supra. In a yeast host, useful promoters are obtained from the *Saccharomyces cerevisiae enolase* (ENO-1) gene, the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423–488.

The nucleic acid sequence encoding said conjugate may also be operably connected to a suitable terminator, such as the human growth hormone terminator (Palmiter et al., Science 222, 1983, pp. 809–814). Preferred terminators for yeast host cells are obtained from the genes encoding *Saccharomyces cerevisiae enolase, Saccharomyces cerevisiae cytochrome C* (CYC1), or *Saccharomyces cerevisiae* glyceraldehyde-3-phosphate dehydrogenase.

The vector may further comprise elements such as polyadenylation signals (e.g., from SV 40 or the adenovirus 5 Elb region), transcriptional enhancer sequences (e.g., the SV 40 enhancer) and translational enhancer sequences (e.g., the ones encoding adenovirus VA RNAs). Useful polyadenylation sequences for yeast host cells are described by Guo and Sherman, 1995, Molecular Cellular Biology 15:5983–5990.

The recombinant expression vector may further comprise a DNA sequence enabling the vector to replicate in the host cell in question. Examples of such a sequence (when the host cell is a mammalian cell) is the SV 40 or polyoma origin of replication. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation to make its function temperature-sensitive in the host cell (see, e.g., Ehrlich, 1978, Proc. Natl. Acad. Sci. USA 75:1433).

The vector may also comprise a selectable marker, e.g., a gene the product of which complements a defect in the host cell, such as the gene coding for dihydrofolate reductase (DHFR) or one which confers resistance to a drug, e.g., neomycin, geneticin, ampicillin, or hygromycin. Suitable markers for yeast host cells are ADE2, HIS3, LEU2, LYS2, MET3, TRP1, and URA3.

The procedures used to ligate the nucleic acid sequences coding for the conjugate, the promoter and the terminator, respectively, and to insert them into suitable vectors containing the information necessary for replication, are well known to persons skilled in the art (cf., for instance, Sambrook et al., op.cit.).

The host cell into which the expression vector is introduced may be any cell which is capable of producing the conjugate and it may be a eukaryotic cell, such as invertebrate cells or vertebrate cells, e.g., *Xenopus laevis oocytes* or mammalian cells, in particular insect and mammalian cells. Examples of suitable mammalian cell lines are the COS, BHK or CHO cell lines. Methods for transfecting mammalian cells and expressing DNA sequences introduced in the cells are described in e.g., Kaufman and Sharp, 1982, J. Mol. Biol. 159:601–621; Southern and Berg, 1982, J. Mol. Appl. Genet. 1:327–341; Loyter et al., 1982, Proc. Natl. Acad. Sci. USA 79:422–426; Wigler et al., 1978, Cell 14:725; Corsaro and Pearson, 1981, Somatic Cell Genetics 7:603; Graham and van der Eb, 1973, Virology 52:456; Fraley et al., 1980, JBC 225:10431; Capecchi, 1980, Cell 22:479; Wiberg et al., 1983,NAR 11:7287; and Neumann et al., 1982, EMBO J. 1:841–845.

The host cell may also be a unicellular pathogen, e.g., a prokaryote, or a non-unicellular pathogen, e.g., a eukaryote. Useful unicellular cells are bacterial cells such as gram positive bacteria including, but not limited to, a *Bacillus* cell or a *Streptomyces* cell, or gram negative bacteria such as *E. coli* and *Pseudomonas sp.* The transformation of a bacterial host cell may, for instance, be effected by protoplast transformation (see, e.g., Chang and Cohen, 1979, Molecular General Genetics 168:111–115), by using competent cells (see, e.g., Young and Spizizin, 1961, Journal of Bacteriology 81:823–829, or Dubnar and Davidoff Abelson, 1971, Journal of Molecular Biology 56:209–221), by electroporation (see, e.g., Shigekawa and Dower, 1988, Biotechniques 6:742–751), or by conjugation (see, e.g., Koehler and Thome, 1987, Journal of Bacteriology 169:5771–5278).

The host cell may be a fungal cell, e.g., *Neurospora, Eupenicillium* (=*Penicillium*), *Emericella* (=*Aspergillus*), *Eurotium* (=*Aspergillus*). The fungal host cell may also be a yeast cell. "Yeast" as used herein includes *ascosporogenous* yeast (*Endomycetales*), *basidiosporogenous* yeast, and yeast belonging to the Fungi Imperfecti (*Blastomycetes*). The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g,. in catalogues of the American Type Culture Collection).

Thus, the invention also relates to a method for producing the peptide conjugate of formula I or III having a natural polypeptide sequence, comprising introducing a nucleic acid sequence encoding a polypeptide sequence comprising the peptide sequence of formula I or III and a selectable marker contained within a nucleic acid construct or a vector into a host cell to obtain a recombinant host cell;

selecting said recombinant host cell;

culturing said recombinant host cells under conditions permitting the production of said polypeptide sequence;

isolating said polypeptide sequence from the culture; and optionally cleaving said polypeptide sequence using an appropriate protease to obtain said peptide conjugate.

The peptide conjugate of formula I or III having a natural polypeptide sequence thus prepared may then be recovered from the culture medium by conventional procedures including separating the host cells from the medium by centrifugation or filtration, precipitating the proteinaceous components of the supernatant or filtrate by means of a salt, e.g., ammonium sulphate, purification by a variety of chromatographic procedures, e.g., ion exchange chromatography, affinity chromatography, or the like. Chemical modification steps to obtain non-natural derivatives may further be employed.

The peptides of the invention may be prepared by methods known per se in the art. Thus, the peptide sequences X and Z may be prepared by standard peptide-preparation techniques such as solution synthesis or Merrifield-type solid phase synthesis. Both the Boc (tert.butyloxycarbonyl) as well as the Fmoc (9-fluorenylmethyloxycarbonyl) strategies are applicable.

Preferred synthetic methods include a method for the preparation of a peptide conjugate of formula IV (X—Z'), comprising the steps of:

a) coupling an amino acid or dipeptide having suitable protecting groups, including an N-α-protecting group, in the activated form to an immobilised peptide sequence H—Z'—SSM, thereby forming an immobilised N-α-protected peptide fragment, b) removing said N-α-protecting group, thereby forming an immobilised protected peptide fragment having an unprotected N-terminal, c) coupling an additional amino acid or dipeptide having suitable protecting groups including an N-α-protecting group in the carboxyl activated form to the N-terminal of the immobilised peptide fragment, and repeating the removal/coupling step procedure in step b) and c) until the desired peptide sequence X is obtained, and then d) cleaving off the peptide conjugate from the solid support material;

and a method for the preparation of a peptide conjugate of formula V (Z—X), comprising the steps of:

a) coupling an amino acid or dipeptide having suitable protecting groups, including an N-α-protecting group, in the activated form to a solid support material (SSM), thereby forming an immobilised protected amino acid or a protected dipeptide, b) removing said N-α-protecting group, thereby forming an immobilised amino acid or peptide fragment having an unprotected N-terminal, c) coupling an additional amino acid or dipeptide having suitable protecting groups, including an N-α-protecting group, in the carboxyl activated form to the N-terminal of the immobilised amino acid or peptide fragment, and repeating the removal/coupling step procedure in step b) and c) until the desired peptide sequence X is obtained, d) coupling an additional amino acid or dipeptide having suitable protecting groups, including an N-α-protecting group, in the carboxyl activated form to the N-terminal of the immobilised peptide fragment, and repeating the removal/coupling step procedure in step b) and d) until the desired peptide sequence Z is obtained, and then e) cleaving off the peptide conjugate from the solid support material.

and, furthermore, a method for the preparation of a peptide conjugate of formula VI (Z-X-Z'), comprising the steps of:

a) coupling an amino acid or dipeptide having suitable protecting groups, including an N-α-protecting group, in the carboxyl activated form to an immobilised peptide sequence H—Z'—SSM, thereby forming an immobilised N-α-protected peptide fragment, b) removing said N-α-protecting group, thereby forming an immobilised peptide fragment having an unprotected N-terminal, c) coupling an additional amino acid or dipeptide having suitable protecting groups, including an N-α-protecting group, in the carboxyl activated form to the N-terminal of the immobilised peptide fragment, and repeating the removal/coupling step procedure in step b) and c) until the desired peptide sequence X is obtained, and then d) coupling an additional amino acid or dipeptide having suitable protecting groups, including an N-α-protecting group, in the carboxyl activated form to the N-terminal of the immobilised peptide fragment, and repeating the removal/coupling step procedure in step b) and d) until the desired peptide sequence Z is obtained, and then e) cleaving off the peptide conjugate from the solid support material.

Experimental Procedures

Apparatus and Synthetic Strategy

Peptides were synthesized batchwise in a polyethylene vessel equipped with a polypropylene filter for filtration using 9-fluorenylmethyloxycarbonyl (Fmoc) as N-α-amino protecting group and suitable common protection groups for side-chain functionalities.

Solvents

Solvent DMF (N,N-dimethylformamide, Riedel de-Häen, Germany) was purified by passing through a column packed with a strong cation exchange resin (Lewatit S 100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O-anion) if free amines are present. Solvent DCM (dichloromethane, analytical grade, Riedel de-Häen, Germany) was used directly without purification. Acetonitril (HPLC-grade, Lab-Scan, Dublin Ireland) was used directly without purification.

Amino Acids

Fmoc-protected amino acids were purchased from Advanced Chem Tech (ACT) in suitabel side-chain protected forms.

Coupling Reagents

Coupling reagent diisopropylcarbodiimide (DIC) was purchased from Riedel de-Häen, Germany.

Solid Supports

Peptides were synthesized on TentaGel S resins 0,22–0,31 mmol/g. TentaGel S-Ram, TentaGel S RAM-Lys(Boc)Fmoc (Rapp polymere, Germany) were used in cases where a C-terminal amidated peptide was preferred, while TentaGel S PHB, TentaGel S PHB Lys(Boc)Fmoc were used when a C-terminal free carboxylic acid was preferred.

Catalysts and Other Reagents

Diisopropylethylamine (DIEA) was purchased from Aldrich, Germany, piperidine and pyridine from Riedel-de Häen, Frankfurt, Germany. Ethandithiol was purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland. Acetic anhydride was obtained from Fluka.

Coupling Procedures

The amino acids were coupled as in situ generated HObt or HOAt esters made from appropriate N-α-protected amino acids and HObt or HOAt by means of DIC in DMF. Acylations were checked by the ninhydrin test performed at 80° C. in order to prevent Fmoc deprotection during the test (Larsen, B. D. and Holm, A., Int. J. Peptide Protein Res. 43, 1994, 1–9).

Deprotection of the N-α-amino Protecting Group (Fmoc)

Deprotection of the Fmoc group was performed by treatment with 20% piperidine in DMF (1×5 and 1×10 min.), followed by wash with DMF (5×15 ml, 5 min. each) until no yellow color could be detected after addition of Dhbt-OH to the drained DMF.

Coupling of HOBt-esters 3 eq. N-α-amino protected amino acid was dissolved in DMF together with 3 eq. HObt and 3 eq DIC and then added to the resin.

Acetylation of the N-terminal Amino Group With Acetic Anhydride 40 eq acetic anhydride was dissolved in DMF together with 5 eq pyridine and then added to the resin.

The acylation was checked by the ninhydrin test as described above.

Trifluoroacetylation of the N-terminal Amino Group With Ethyl Trifluoroacetate 30 eq ethyl trifluoroacetate was dissolved in dichloromethane together with 10 eq triethyl amine and then added to resin. The acylation was checked by ninhydrin test as described above.

Cleavage of Peptide From Resin With Acid

Peptides were cleaved from the resins by treatment with 95% triflouroacetic acid (TFA, Riedel-de Häen, Frankfurt, Germany)-water v/v or with 95% TFA and 5% ethandithiol v/v at r.t. for 2 h. The filtered resins were washed with 95% TFA-water and filtrates and washings evaporated under reduced pressure. The residue was washed with ether and freeze dried from acetic acid-water. The crude freeze dried product was analyzed by high-performance liquid chromatography (HPLC) and identified by mass spectrometry (MS).

Batchwise Peptide Synthesis on TentaGel Resin (PEG-PS)

TentaGel resin (1 g, 0.23–0.24 mmol/g) was placed in a polyethylene vessel equipped with a polypropylene filter for filtration. The resin was swelled in DMF (15 ml), and treated with 20% piperidine in DMF in order to remove the initial Fmoc group either on the linker TentaGel S RAM or on the first amino acid on the resin TentaGel S RAM-Lys(Boc) Fmoc. The resin was drained and washed with DMF until no yellow color could be detected after addition of Dhbt-OH to the drained DMF. The amino acids according to the sequence were coupled as preformed Fmoc-protected HObt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test as described above. After completed synthesis the peptide-resin was washed with DMF (3×15 ml, 5 min each), DCM (3×15 ml, 1 min each) and finally diethyl ether (3×15 ml, 1 min each) and dried in vacuo. The peptide was cleaved from the resin as described earlier and the crude peptide product was analysed and purified as described below HPLC Conditions Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition. The following columns and HPLC buffer system was used:

Column: VYDAC 238TP5415, C-18, 5 mm, 300 Å 150× 4.6 mm.

Buffers: A: 0,1% TFA in MQV; B: 0,085% TFA, 10% MQV, 90% MeCN.

Gradient: 0–1,5 min. 0% B 1,5–25 min 50% B

25–30 min 100% B

30–35 min 100% B

35–40 min 0% B

Flow 1, ml/min, oven temperature 40° C., UV detection: I=215 nm.

HPLC purification of the crude peptide

The crude peptide products were purified PerSeptive Biosystems VISION Workstation. VISION 3.0 software was used for instrument control and data acquisition. The following column and HPLC buffer system was used:

Column: Kromasil KR 100 Å, 10 mm C-8,250×50.8 mm.

Buffer system: Buffers: A: 0,1% TFA in MQV; B: 0,085% TFA, 10% MQV, 90% MeCN.

Gradient: 0–37 min. 0–40% B

Flow 35 ml/min, UV detection: I=215 nm and 280 nm.

Mass Spectroscopy

The peptides were dissolved in super gradient methanol (Labscan, Dublin, Ireland), milli-Q water (Millipore, Bedford, Mass.) and formic acid (Merck, Damstadt, Germany) (50:50:0.1 v/v/v) to give concentrations between 1 and 10 mg/ml. The peptide solutions (20 ml) were analysed in positive polarity mode by ESI-TOF-MS using a LCT mass spectrometer (Micromass, Manchester, UK).

Antibody Preparation And Use

Antibodies of the invention can be prepared by techniques generally known in the field. Preferred antibodies are generated to a purified sample of peptide or peptide conjugate antigen. Suitable peptide and peptide conjugate antigens for making such antibodies are disclosed throughout the application including Examples 22–23, below. Although most polyclonal antibodies of the invention feature exceptionally good and specific binding, for some applications it may be as useful or more useful to employ monoclonal antibodies. See generally Harlow, E and D. Lane in *Antibodies: A Laboratory Manual*, Cold Spring Harbor, N.Y. (disclosing methods for making and using polyclonal and monoclonal antibodies).

Generally, antibodies can be prepared by immunizing a mammal with a purified or semi-purified sample of the peptide or peptide conjugate antigen as provided herein, alone or complexed with a carrier. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection. The optimal immunizing interval, immunizing dose, etc. can vary within relatively wide ranges and can be determined empirically based on this disclosure. Typical procedures involve injection of the antigen several times over a number of months. Antibodies are collected from serum of the immunized animal by standard techniques and screened to find antibodies specific for the peptide or peptide conjugate antigen used. Monoclonal antibodies can be produced in cells which produce antibodies and those cells used to generate monoclonal antibodies by using standard fusion techniques for forming hybridoma cells. See G. Kohler, et al., *Nature,* 256:456 (1975). Typically this involves fusing an antibody producing cell with an immortal cell line such as a myeloma cell to produce the hybrid cell. Alternatively, monoclonal antibodies can be produced from cells by the method of Huse, et al., *Science,* 256:1275 (1989).

See also Harlow, E. and D. Lane, *supra,* for additional information relating to making and using polyclonal and monoclonal antibodies. A variety of suitable antibody purification strategies are reported which can be used in accord with this invention.

In embodiments in which monoclonal antibodies are desired, one suitable protocol provides for intraperitoneal immunization of a mouse with a composition comprising purified peptide conjugate conducted over a period of about two to seven months. Spleen cells then can be removed from the immunized mouse. Sera from the immunized mouse is assayed for titers of antibodies specific for a particular peptide conjugate prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT) or thymidine kinase deficiency (TK$^-$). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. See G. Kohler, et al., *Nature, supra.* The thus cloned hybridoma is grown in a culture medium, e.g. RPMI-1640. See G. E. More, et al., *Journal of American Medical Association,* 199:549 (1967). Hybridomas, grown after the fusion procedure, are screened such as by radioimmunoassay or enzyme immunoassay for secretion of antibodies that bind specifically to the antigen employed e.g. antibodies are selected that bind to the purified peptide conjugate but not to other unrelated control peptides. Preferably an ELISA or related immunological assay is employed for the screen. Hybridomas that show positive results upon such screening can be expanded and cloned by limiting dilution method. Further screens are preferably performed to select antibodies that can bind to peptide conjugate in solution. The isolated antibodies can be further purified by nearly any suitable immunological technique including affinity chromatography.

The molecular weight of the antibodies of the invention will vary depending on several factors such as the intended use and whether the antibody includes a conjugated or recombinantly fused toxin, pharmaceutical, or detectable label or the like. In general, an antibody of the invention will have a molecular weight of between approximately 20 to 150 kDa. Such molecular weights can be readily are determined by molecular sizing methods such as SDS-PAGE gel electrophoresis followed by protein staining or Western blot analysis.

Preferred peptide conjugates for making polyclonal antibodies of the invention are disclosed eg., in Examples 22–23.

By the phrase "specific binding" or related phrase as it relates to association between an antibody and peptide or peptide conjugate antigen is meant that the antibody forms an immune complex with the particular antigen and not with other antigens (such as related or unrelated peptide conjugates). Methods for detecting and optionally quantifying such specific binding include standard immmunoassays eg., ELISA, antibody capture and antigen capture assays.

Preferred antibodies of the invention specifically bind a subject peptide or peptide conjugate antigen. See Example 23 below, for instance.

The following examples are provided to point out preferred aspects of the invention and are not intended to be indicative of the scope of the invention.

SYNTHESIS EXAMPLES

Example 1

Synthesis of Compound 1 Ac-Arg-Tyr-Tyr-Arg-Trp-Lys-Lys-Lys-Lys-Lys-Lys-Lys-NH$_2$ (SEQ ID NO:35) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 390 mg. After purification using preparativ HPLC as earlier described, 210 mg peptide product was collected with a purity better than 95% and the identity of the peptide was confirmed by MS (found M 1780.25, calculated M 1780.11).

Example 2

Synthesis of Compound 1A Ac-Arg-Tyr-Tyr-Arg-Trp-Lys-Lys-Lys-Lys-Lys-Lys-Lys-NH$_2$ (SEQ ID NO:35)×9 AcOH (acetate salt)

Counter Ion Exchange From Trifluoroacetate To Acetate of Compound 1

The purified synthetic peptide product of compound 1 is isolated as a trifluoroacetate salt, Ac-Arg-Tyr-Tyr-Arg-Trp-Lys-Lys-Lys-Lys-Lys-Lys-Lys-NH2 (SEQ ID NO:35)×9 TFA, due to the presence of trifluoroacetic acid (0,1% v/v) in the HPLC buffers used for the purification of the crude synthetic peptide product.

In order to exchange the counter ion trifluoroacetate with acetate, a solution of the peptide was passed through a column packed with strong base ion exchange resin on the acetate (Dowex 1×8).

1 g Compound 1 is dissolved in 40 ml water. The solution is passed through a column containing 40 ml strong base ion exchange resin on the acetate (Dowex 1×8; capacity 1.33 meq/ml resin). The resin is then washed with 4×30 ml water and the eluate is collected and lyophilized resulting in 792 mg acetate salt (hygroscopic) with a purity according to HPLC analysis of 98%.

Example 3

Synthesis of Compound 1C Ac-Arg-Tyr-Tyr-Arg-Trp-Lys-Lys-Lys-Lys-Lys-Lys-Lys-NH$_2$ (SEQ ID NO:35)×9 HCI (chloride salt)

Counter Ion Exchange From Trifluoroacetate (Tfa) To Chloride (Cl—) of Compound 1

100 mg Compound 1 was dissolved in 50 ml 0.1 M hydrochloric acid and the resulting solution was lyophilized.

The remanence was dissolved in 50 ml water and lyophilized again resulting in 74 mg of the chloride salt with a purity according to HPLC of 97%.

Example 4

Synthesis of Compound 2 Ac-Lys-Lys-Lys-Lys-Lys-Lys-Arg-Tyr-Tyr-Arg-Trp-Lys-NH₂ (SEQ ID NO:42) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Lysine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 231 mg. After purification using preparativ HPLC as described above, 126 mg peptide product was collected with a purity better than 93% and the identity of the peptide was confirmed by MS (found M 1780,25, calculated M 1780,11).

Example 5

Synthesis of Compound 3 H-Asn-Glu-Glu-Glu-Glu-Glu-Arg-Tyr-Tyr-Arg-Trp-Lys-Lys-Lys-Lys-Lys-Lys-Lys-NH₂ (SEQ ID NO:33) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Asparagine. All couplings were continued over night. The acylations were checked as earlier described. After completed synthesis the peptide was cleaved from the resin as described above. Yield of crude product 212 mg. After purification using preparativ HPLC as described above, 112 mg peptide product was collected with a purity better than 98% and the identity of the peptide was confirmed by MS (found M 2497,25 calculated M 2497,35).

Example 6

Synthesis of Compound 4 Ac-Arg-Tyr-Asn-Arg-Trp-Lys-Lys-Lys-Lys-Lys-Lys-Lys-NH₂ (SEQ ID NO:50) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 502 mg. After purification using preparativ HPLC as earlier described, 272 mg peptide product was collected with a purity better than 98% and the identity of the peptide was confirmed by MS (found M 1731.25, calculated M 1731.09).

Example 7

Synthesis of Compound 5 Ac-Lys-Lys-Lys-Lys-Lys-Lys-Lys-Trp-Arg-Tyr-Tyr-Asn-NH₂ (SEQ ID NO:51) on TentaGel S RAM Dry TentaGel S RAM (0.24 mmol/g, 1 g) was placed in a polyethylene vessel equipped with a polypropylene filter for filtration and treated as described under "batchwise peptide synthesis on TentaGel resin" until finishing the coupling of the N-terminal Lysine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 586 mg. After purification using preparativ HPLC as earlier described, 365 mg peptide product was collected with a purity better than 99% and the identity of the peptide was confirmed by MS (found M 1738.0, calculated M 1738.05).

Example 8

Synthesis of Compound 6 Ac-Lys-Lys-Lys-Lys-Lys-Lys-Lys-Trp-Arg-Tyr-Tyr-Arg-NH₂ (SEQ ID NO:52) on TentaGel S RAM Dry TentaGel S RAM (0.23 mmol/g, 1 g) was placed in a polyethylene vessel equipped with a polypropylene filter for filtration and treated as described under "batchwise peptide synthesis on TentaGel resin" until finishing the coupling of the N-terminal Lysine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 437 mg. After purification using preparativ HPLC as earlier described, 257 mg peptide product was collected with a purity better than 98% and the identity of the peptide was confirmed by MS (found M 1780.0, calculated M 1780.11).

Example 9

Synthesis of Compound 7 Ac-D-Lys-D-Lys-D-Lys-D-Lys-D-Lys-D-Lys-D-Lys-D-Trp-D-Arg-D-Tyr-D-Tyr-D-Arg-NH₂ (SEQ ID NO:on TentaGel S RAM Dry TentaGel S RAM (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Lysine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 410 mg. After purification using preparativ HPLC as earlier described, 263 mg peptide product was collected with a purity better than 98% and the identity of the peptide was confirmed by MS (found M 1780.13, calculated M 1780.11).

Example 10

Synthesis of Compound 8 Ac-D-Arg-D-Tyr-D-Tyr-D-Arg-D-Trp-D-Lys-D-Lys-D-Lys-D-Lys-D-Lys-D-Lys-D-Lys-NH₂ on TentaGel S RAM Dry TentaGel S RAM (0.23 mmol/g,1 g) was placed in a polyethylene vessel equipped with a polypropylene filter for filtration and treated as described under "batchwise peptide synthesis on TentaGel resin" until finishing the coupling of the N-terminal D-Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 419 mg. After purification using preparativ HPLC as earlier described, 205 mg peptide product was collected with a purity better than 97% and the identity of the peptide was confirmed by MS (found M 1780.0, calculated M 1780.11).

Example 11

Synthesis of Compound 9 Ac-Lys-Tyr-Tyr-Arg-Trp-Lys-Lys-Lys-Lys-Lys-Lys-NH$_2$ ( SEQ ID NO:53) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Lysine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 445 mg. After purification using preparativ HPLC as earlier described, 287 mg peptide product was collected with a purity better than 96% and the identity of the peptide was confirmed by MS (found M 1752.0, calculated M 1752.1).

Example 12

Synthesis of Compound 10 Ac-Arg-Tyr-Tyr-Arg-Ile-Lys-Lys-Lys-Lys-Lys-Lys-NH$_2$ (SEQ ID NO:41) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 376 mg. After purification using preparativ HPLC as earlier described, 134 mg peptide product was collected with a purity better than 97% and the identity of the peptide was confirmed by MS (found M 1707.0, calculated M 1707.11).

Example 13

Synthesis of Compound 11 Ac-Arg-Tyr-Tyr-Arg-Trp-Lys-Ala-Lys-Lys-Lys-Lys-Lys-NH$_2$ (SEQ ID NO:54) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 429 mg. After purification using preparativ HPLC as earlier described, 260 mg peptide product was collected with a purity better than 96% and the identity of the peptide was confirmed by MS (found M 1723.0, calculated M 1723.05).

Example 14

Synthesis of Compound 12 Ac-Arg-Tyr-Tyr-Arg-Trp-Lys-Lys-Lys-Lys-Lys-Lys-NH$_2$ (SEQ ID NO:55) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 426 mg. After purification using preparativ HPLC as earlier described, 266 mg peptide product was collected with a purity better than 98% and the identity of the peptide was confirmed by MS (found M 1651.88, calculated M 1652.01).

Example 15

Synthesis of Compound 13 Ac-Arg-Tyr-Tyr-Arg-Trp-Lys-Lys-Lys-Lys-Lys-Lys-Cys-NH$_2$ (SEQ ID NO:56) on TentaGel S RAM Dry TentaGel S RAM (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 465 mg. After purification using preparativ HPLC as earlier described, 313 mg peptide product was collected with a purity better than 91% and the identity of the peptide was confirmed by MS (found M 1883.0, calculated M 1883.12).

Example 16

Synthesis of Compound 15 Ac-Arg-Tyr-Tyr-Arg-Trp-Lys-Cys-NH$_2$ (SEQ ID NO:59) on TentaGel S RAM Dry TentaGel S RAM (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 249 mg. After purification using preparativ HPLC as earlier described, 190 mg peptide product was collected with a purity better than 94% and the identity of the peptide was confirmed by MS (found M 1114.50, calculated M 1114.55).

Example 17

Synthesis of Compound 16 H-Cys-Ala-Pro-Pro-Ser-Lys-Lys-Lys-Lys-Lys-NH$_2$ (SEQ ID NO:64) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Cysteine. All couplings were continued over night. The acylations were checked as earlier described. After the final deprotection of the Fmoc group the peptide was cleaved from the resin as described above. Yield of crude product 359 mg. After purification using preparativ HPLC as earlier described, 242 mg peptide product was collected with a purity better than 98% and the identity of the peptide was confirmed by MS (found M 1240.76, calculated M 1240.78).

Example 18

Synthesis of Compound 17 H-Cys-Lys-Lys-Lys-Lys-Lys-Lys-NH$_2$ (SEQ ID NO:62) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Cysteine. All couplings were continued over night. The acylations were checked as earlier described. After the final deprotection of the Fmoc group the peptide was cleaved from the resin as described above. Yield of crude product 287 mg. After purification using preparativ HPLC as earlier described, 205 mg peptide product was collected with a purity better than 90% and the identity of the peptide was confirmed by MS (found M 888.5, calculated M 888.61).

Example 19

Synthesis of Compound 18 Ac-Arg-Tyr-Tyr-Arg-Trp-Lys-Lys-Lys-Lys-Lys-Lys-Cys-NH$_2$ (SEQ ID NO:56) on TentaGel S RAM Dry TentaGel S RAM (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 465 mg. After purification using preparativ HPLC as earlier described, 313 mg peptide product was collected with a purity better than 91% and the identity of the peptide was confirmed by MS (found M 1883.00, calculated M 1883.12).

Example 20

Synthesis of Compound 14 Tfa-Arg-Tyr-Tyr-Arg-Trp-Lys-Lys-Lys-Lys-Lys-Lys-NH$_2$ (SEQ ID NO:35) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was trifluoroacetylated as described above. The reaction was continued over night. The acylations were checked as earlier described. After completed synthesis the peptide was cleaved from the resin as described above. Yield of crude product 392 mg. After purification using preparativ HPLC as earlier described, 105 mg peptide product was collected with a purity better than 96% and the identity of the peptide was confirmed by MS (found M 1834.25, calculated M 1834.08).

Example 21

Synthesis of Compound CE1 Ac-Arg-Tyr-Tyr-Arg-Trp-Lys-NH$_2$ (SEQ ID NO:1) on TentaGel S RAM-Lys(Boc)Fmoc Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Arginine. All couplings were continued over night. After deprotection of the Fmoc group the N-terminal amino group was acetylated as described above. The coupling was continued over night. The acylations were checked as earlier described. After completed synthesis the peptide was cleaved from the resin as described above. Yield of crude product 143 mg. After purification using preparativ HPLC as earlier described, 52 mg peptide product was collected with a purity better than 97% and the identity of the peptide was confirmed by MS (found M 1011.54, calculated M 1011.54).

Example 22

Immunogen Production

Antibodies specific for Compound 1 have been raised by conjugating peptides corresponding to the N-terminus (Ac-RYYRWKC-NH$_2$) (SEQ ID NO:59), the C-terminus (H-CAPPSKKKKKK-NH$_2$) (SEQ ID NO:64) and Compound 13 which is a full length molecule having a terminal Cys residue to accomodate the coupling chemistry (Ac-RYYRWKKKKKKKC-NH$_2$) (SEQ ID NO:56). Ac-RYYRWKC-NH$_2$ and H-CAPPSKKKKKK-NH$_2$ (SEQ ID NO:64) were coupled to keyhole limpet hemocyanin (KLH) and a commercially available cationised bovine serum albumin (Supercarrier, Pierce Chemical). The resulting KLH and Supercarrier conjugates were combined, and injected into rabbits. Compound 13 was conjugated to purified protein derivative (PPD) and injected into a BCG primed goat. Immunisations followed standard protocols of initial immunisation of immunogen in an emulsion of Freund's complete adjuvant followed by a regimen of boosting with an emulsion of the immunogen in Freund's incomplete adjuvant and test bleeding until antibody titers were at acceptable levels. The antibodies were purified in one step by affinity chromatography on a protein G column specific for the IgG subclass of immunoglobulins.

Example 23

Antibody Production

Antibodies were prepared generally along lines discussed previously. Four representative polyclonal antibodies have been raised to peptides fitting the general formulas described in the claims. These comprise a peptide incorporating the sequence of N-terminus of compound 1, two peptides incorporating the sequence of the C-terminus of compound 1, as well as a peptide incorporating the full sequence of compound 1. These peptides are designated compounds 15, 16, 17, or 18, respectively, and have the following sequences: Ac-RYYRWKKKKKKKC-NH$_2$ (SEQ ID NO:56) (compound 15); CAPPSKKKKKK-NH$_2$ (SEQ ID NO:64) (compound 16); CKKKKKK-NH$_2$ (SEQ ID NO:62) (compound 17) and Ac-RYYRWKKKKKKKC-NH$_2$ (SEQ ID NO:56) (compound 18). Polyclonal antibodies to compounds 15, 16, and 17 were raised in rabbits, and to compound 18 in goat. These polyclonal antibodies are highly specific and result in titers listed in the accompanying table when the antibodies are evaluated in a standard ELISA type assay employing Compound 1 as the antigen and utilizing calorimetric detection of bound antibody by a commercially available HRP-conjugated anti-IgG antibody. Preliminary testing for several of the antibodies has also indicated the lack of cross reaction with antigens of low sequence similarity to compound 1 in the standard ELISA assay described above. Table 7 is shown below.

TABLE 7

| Immunogen | Antigen in ELISA | Antibody titer |
| --- | --- | --- |
| 15 | Compound 1 | 1:750,000 |
| 16 | Compound 1 | 1:200,000 |
| 17 | Compound 1 | 1:350,000 |
| 17 | Glucagon | No Reaction |
| 18 | Compound 1 | 1:2000 |

See the Examples and discussion above for more information relating to the peptide conjugate compounds disclosed in this Example.

All references disclosed in this application are incorporated herein by reference.

While the invention has been described with reference to specific embodiments, modifications and variations of the invention may be constructed without departing from the scope of the invention, which is defined in the following claims.

What is claimed is:

1. A peptide conjugate having the following formula:

$R_1$-Arg-Tyr-Tyr-Arg-Trp-Lys-Lys-Lys-Lys-Lys-Lys-Lys-$R_2$, wherein $R_1$ represents hydrogen, acyl, acetyl, or a trifluoroacetyl group and $R_2$ represents hydroxyl or $NR_3R_4$ in which each of $R_3$ and $R_4$ independently represents hydrogen, C(1–6) alkoxy, C(1–6) aryloxy, or C(1–6) lower alkyl; and a salt, hydrate, or a solvate thereof.

2. A solution comprising a peptide conjugate having the following formula:

$R_1$-Arg-Tyr-Tyr-Arg-Trp-Lys-Lys-Lys-Lys-Lys-Lys-Lys-$R_2$, wherein $R_1$ represents hydrogen, acyl, acetyl, or a trifluoroacetyl group and $R_2$ represents hydroxyl or $NR_3R_4$ in which each of $R_3$ and $R_4$ independently represents hydrogen, C(1–6) alkoxy, C(1–6) aryloxy, or C(1–6) lower alkyl; and a salt, hydrate, or a solvate thereof, wherein the solution is sterile.

3. A peptide conjugate having the following formula:

Ac-Arg-Tyr-Tyr-Arg-Trp-Lys-Lys-Lys-Lys-Lys-Lys-Lys-$NH_2$; and a salt, hydrate, or a solvate thereof.

4. A solution comprising a peptide conjugate having the following formula:

Ac-Arg-Tyr-Tyr-Arg-Trp-Lys-Lys-Lys-Lys-Lys-Lys-Lys-$NH_2$; and a salt, hydrate, or a solvate thereof, wherein the solution is sterile.

5. A composition comprising a peptide conjugate having the following formula:

$R_1$-Arg-Tyr-Tyr-Arg-Trp-Lys-Lys-Lys-Lys-Lys-Lys-Lys-$R_2$, wherein $R_1$ represents hydrogen, acyl, acetyl, or a trifluoroacetyl group and $R_2$ represents hydroxyl or $NR_3R_4$ in which each of $R_3$ and $R_4$ independently represents hydrogen, C(1–6) alkoxy, C(1–6) aryloxy, or C(1–6) lower alkyl; and a salt, hydrate, or a solvate thereof, the composition further comprising a pharmaceutically acceptable carrier or diluent.

6. The composition of claim 5, wherein the pharmaceutically acceptable carrier is a solid, the composition being in a tablet form.

7. The composition of claim 5, wherein the diluent is a liquid comprising isotonic saline.

8. A peptide conjugate having the following formula:

$R_1$-Arg-Tyr-Tyr-Arg-Trp-Z-$R_2$, wherein $R_1$ represents hydrogen, acyl, acetyl, or a trifluoroacetyl group, Z represents $(Lys)_{11}$, $(Lys)_{10}$, $(Lys)_9$, $(Lys)_8$, $(Lys)_6$, or $(Lys)_5$ and $R_2$ represents hydroxyl or $NR_3R_4$ in which each of $R_3$ and $R_4$ independently represents hydrogen, C(1–6) alkoxy, C(1–6) aryloxy, or C(1–6) lower alkyl; and a salt, hydrate, or a solvate thereof.

9. A composition comprising a peptide conjugate having the following formula:

$R_1$-Arg-Tyr-Tyr-Arg-Trp-Z-$R_2$, wherein $R_1$ represents hydrogen, acyl, acetyl, or a trifluoroacetyl group, Z represents $(Lys)_{11}$, $(Lys)_{10}$, $(Lys)_9$, $(Lys)_8$, $(Lys)_6$, $(Lys)_5$ and $R_2$ represents hydroxyl or $NR_3R_4$ in which each of $R_3$ and $R_4$ independently represents hydrogen, C(1–6) alkoxy, C(1–6) aryloxy, or C(1–6) lower alkyl; and a salt, hydrate, or a solvate thereof.

10. The composition of claim 9, wherein the composition further comprises a pharmaceutically acceptable carrier or diluent.

11. The composition of claim 10, wherein the pharmaceutically acceptable carrier is a solid, the composition being in a tablet form.

12. The composition of claim 10, wherein the pharmaceutically acceptable carrier is a liquid comprising isotonic saline.

13. A solution comprising a peptide conjugate having the following formula:

$R_1$-Arg-Try-Tyr-Arg-Trp-Z-$R_2$, wherein, $R_1$ represents hydrogen, acyl, acetyl, or a trifluoroacetyl group, Z represents $(Lys)_{11}$, $(Lys)_{10}$, $(Lys)_9$, $(Lys)_8$, $(Lys)_6$, or $(Lys)_5$ and $R_2$ represents hydroxyl or $NR_3R_4$ in which each of $R_3$ and $R_4$ independently represents hydrogen, C(1–6) alkoxy, C(1–6) aryloxy, or C(1–6) lower alkyl; and a salt, hydrate, or a solvate thereof, wherein the solution is sterile.

14. A peptide conjugate having the following formula:

Ac-Arg-Tyr-Tyr-Arg-Trp-Z-$NH_2$, wherein, Z represents $(Lys)_{11}$, $(Lys)_{10}$, $(Lys)_9$, $(Lys)_8$, $(Lys)_6$, or $(Lys)_5$ and a salt, hydrate, or a solvate thereof.

15. A composition comprising a peptide conjugate having the following formula:

Ac-Arg-Tyr-Tyr-Arg-Trp-Z-$NH_2$, wherein, Z represents $(Lys)_{11}$, $(Lys)_{10}$, $(Lys)_9$, $(Lys)_8$, $(Lys)_6$, $(Lys)_5$; and a salt, hydrate, or a solvate thereof.

16. The composition of claim 15, wherein the composition further comprises a pharmaceutically acceptable carrier or diluent.

17. The composition of claim 16, wherein the pharmaceutically acceptable carrier is a solid, the composition being in a tablet form.

18. The composition of claim 16, wherein the diluent is a liquid comprising isotonic saline.

19. A solution comprising a peptide conjugate having the following formula:

Ac-Arg-Tyr-Tyr-Arg-Trp-Z-$NH_2$, wherein, Z represents $(Lys)_{11}$, $(Lys)_{10}$, $(Lys)_9$, $(Lys)_8$, $(Lys)_6$, $(Lys)_5$; and a salt, hydrate, or a solvate thereof, wherein the solution is sterile.

* * * * *

UNITED STATES PATENT AND TRADEMARK OFFICE
CERTIFICATE OF CORRECTION

PATENT NO. : 7,244,701 B2 Page 1 of 1
APPLICATION NO. : 09/882291
DATED : July 17, 2007
INVENTOR(S) : Larsen et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 16 days Delete the phrase "by 16 days" and insert -- by 24 days --

Signed and Sealed this

Eleventh Day of March, 2008

JON W. DUDAS
*Director of the United States Patent and Trademark Office*